United States Patent
Pon

[19]

[11] Patent Number: 5,922,557

[45] Date of Patent: *Jul. 13, 1999

[54] SYSTEM FOR STABLY EXPRESSING A HIGH-AFFINITY CAMP PHOSPHODIESTERASE AND USE THEREOF

[75] Inventor: Douglas J. Pon, Dorval, Canada

[73] Assignee: Merck & Co., Inc., Rahway, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/003,626

[22] Filed: Jan. 7, 1998

Related U.S. Application Data

[60] Provisional application No. 60/034,691, Jan. 9, 1997, and provisional application No. 60/065,420, Nov. 13, 1997.

[51] Int. Cl.$^6$ .............................. C12Q 1/42; C12Q 1/44; C12Q 1/00

[52] U.S. Cl. .................................. 435/21; 435/19; 435/4; 435/7.6

[58] Field of Search ................... 435/21, 19, 4, 435/7.6

[56] References Cited

U.S. PATENT DOCUMENTS

| | | | |
|---|---|---|---|
| 5,591,776 | 1/1997 | Cavalla et al. | 514/622 |
| 5,665,737 | 9/1997 | Cavalla et al. | 514/338 |
| 5,665,754 | 9/1997 | Feldman et al. | 514/397 |
| 5,710,170 | 1/1998 | Guay et al. | 514/332 |
| 5,744,473 | 4/1998 | Chasin et al. | 514/262 |

FOREIGN PATENT DOCUMENTS

| | | |
|---|---|---|
| WO94/14742 | 7/1994 | WIPO . |
| WO94/20079 | 9/1994 | WIPO . |
| WO95/00139 | 1/1995 | WIPO . |
| WO95/35285 | 12/1995 | WIPO . |
| WO96/20281 | 7/1996 | WIPO . |
| WO97/22585 | 6/1997 | WIPO . |

*Primary Examiner*—Louise N. Leary
*Attorney, Agent, or Firm*—Richard C. Billups; David L. Rose

[57] ABSTRACT

A CHO-K1 cell line stably expressing a recombinant full-length human PDE IVa (rhPDEIVa) enzyme was established under hygromycin B selection. Inhibition of the expressed PDE IVa activity by selective PDE IV inhibitors was evaluated. The rank order of potencies of the inhibitors in elevating cAMP in the whole-cell assay was quite different from that on the soluble enzyme. The whole-cell rank order of potencies was also maintained when PKA activity ratios were measured in place of cAMP levels. When inhibition of soluble PDE IVa activity was examined in the presence of 100 mM $MgCl_2$, the rank order of potencies of the inhibitors mirrored that obtained for the whole-cell assays (both cAMP and PKA). The observed "high-affinity" conformation of the enzyme was not dependent upon a specific cation or anion. The shift in sensitivity of the rhPDE IVa enzyme for (R)-rolipram in the presence of increased ionic strength was accompanied by an enhanced capacity of the soluble enzyme preparation to specifically bind [3H](R)-rolipram with high-affinity.

15 Claims, 18 Drawing Sheets

SYSTEM FOR STABLY EXPRESSING A HIGH-AFFINITY CAMP PHOSPHODIESTERASE AND USE THEREOF

This application claims benefit of USC Provisional appl. Ser. No. 60/034,691, filed Jan. 9, 1997 and Provisional appl. Ser. No. 60/065,420, filed Nov. 13, 1997.

BACKGROUND OF THE INVENTION

This invention related to a system for stably expressing a low-Km cAMP phosphodiesterase (PDE) and the use of the system for assessing inhibitors of PDE. In particular, this invention related to a system for the stable expression of a low-Km PDE IV and the use of the stable system in the evaluation of inhibitors of PDE IV. This invention also relates to an improved in vitro assay for the evaluation of inhibitors of PDE IV directed against a "high-affinity" state enzyme with respect to rolipram.

Phosphodiesterases (PDEs) are a family of enzymes that metabolize 3',5' cyclic nucleotides to inactive metabolites, thereby terminating their second messenger role in mediating the cellular responses to various hormones and neurotransmitters. To date, seven families of PDE enzymes have been identified and each isoenzyme has been mapped to a distinct gene locus. These isoenzymes exhibit different substrate specificities for cAMP and/or cGMP, catalytic activities, tissue and cellular distributions, and sensitivity to different endogenous activators and inhibitors. In addition, selective inhibitors of some of these isoenzymes have been synthesized, and have been validated as useful tools for examining the biological function(s) of these enzymes in various tissues (See reference (1)).

Recently, the low-Km cAMP specific, type IV PDE family of enzymes has generated considerable interest as potential targets for the development of novel antiasthmatic and antiinflammatory drugs (2). Within this family of PDEs exist at least four isoenzymes, each of which is encoded by a distinct gene (3). Additionally, the mRNA of each gene product is thought to undergo alternative splicing, thereby giving rise to isoforms for each isoenzyme, respectively (4,5). The four known PDE IV gene products (a,b,c,d) exhibit different tissue distributions (6), but in general are expressed in a wide number of cells that play a role in allergic and inflammatory responses (7). Investigators have utilized rolipram and Ro 20-1724, both potent and selective prototypic inhibitors of the PDE IV enzyme, to examine the effect of PDE IV inhibition on the activation state of inflammatory cells. Inhibitors of PDE IV enzyme(s) have been shown to block antigen-induced airway eosinophilia in allergic guinea pigs (8), inhibit superoxide production by human neutrophils (9), suppress LPS induction of TNFa release from human monocytes (10), inhibit arachidonate release from human neutrophils (11) and to block ozone-induced airways hyperreactiviy in a variety of species (12).

To date, the potentially attractive antiasthmatic and anti-inflammatory properties of drugs that inhibit PDE IV enzymes have been offset by their ability to cause gastrointestinal discomfort (13), and CNS hyperactivity (14). More importantly, however, the potency of this class of drug appears to track with its propensity to cause nausea and vomiting in the clinical setting. These dose limiting side effects have precluded the clinical development of many potent and potentially therapeutically useful PDE IV enzyme inhibitors.

In addition to the pronounced clinical side effects exhibited by PDE IV inhibitors, problems exist with the mechanistic basis by which these compounds are thought to act. Alterations in cellular function by these compounds are expected to be accompanied by increases in the cellular content of cAMP. Examples have been reported in the literature demonstrating a lack of correlation between elevations in cAMP and endpoint cellular measurements (16,17, 18). Additionally, the potency of these compounds in elevating cellular cAMP in the target cell does not always translate biochemically into their ability to inhibit the PDE IV enzyme in a broken cell preparation.

Herein we report the establishment and characterization of a CHO-K1 cell line which stably expresses high levels of a full length low-Km cAMP specific PDE IVa enzyme. We have examined several well known potent PDE IV enzyme inhibitors and have compared the rank order of their potencies in elevating cAMP in a whole-cell preparation with their ability to inhibit phosphodiesterase activity in a broken-cell preparation.

We have surprisingly found that the soluble enzyme inhibition assay described in the prior art does not reflect behavior of the inhibitors acting in vivo. We have developed an improved soluble enzyme assay which is superior in terms of it ability to reflect the behavior of inhibitors acting in vivo. We have also developed a the whole-cell assay which reflects the behavior of inhibitors acting in vivo.

SUMMARY OF THE INVENTION

This invention related to a system for stably expressing a low-Km cAMP phosphodiesterase (PDE) and the use of the system for assessing inhibitors of PDE. In particular, this invention related to a system for the stable expression of a low-Km cAMP PDE IV and the use of the stable system in the evaluation of inhibitors of PDE IV. This invention also relates to an improved in vitro assay for the evaluation of inhibitors directed against a "high-affinity" state of the enzyme with respect to rolipram.

A CHO-K1 cell line stably expressing a recombinant full-length human PDE IVa (rhPDEIVa) enzyme was established under hygromycin B selection. Full-length expression of the protein was determined by Western blot analysis which revealed the presence of a 117 kDa immunoreactive band using rabbit anti-PDE IVa antibodies. The potency of inhibitor compounds was examined by their ability to increase cAMP in the whole-cell, and by their ability to inhibit cAMP hydrolysis in a 100,000×g supernatant (soluble enzyme preparation) obtained from the same cell line. Inhibition of the expressed PDE IVa activity by selective PDE IV inhibitors (R) and (S)-rolipram, RS 14203, and CDP 840) at 100 nM substrate demonstrated that RS 14203 and CDP 840 were the most potent with $IC_{50}$=9 nM, followed by (R)-rolipram ($IC_{50}$=110 nM) and (S)-rolipram ($IC_{50}$=420 nM). The rank order of potencies of the inhibitors in elevating cAMP in the whole-cell assay was quite different from that on the soluble enzyme. RS 14203 was still the most potent compound in elevating cAMP. Moreover, the relative rank order of potencies between CDP 840 and (R)-rolipram changed dramatically, such that (R)-rolipram was more potent than CDP 840=(S)-rolipram. An apparent 30-fold stereoselectivity between (R)- and (S)-rolipram was also noted. The whole-cell rank order of potencies was also maintained when PKA activity ratios were measured in place of cAMP levels. When inhibition of soluble PDE IVa activity was examined in the presence of 100 mM $MgCl_2$, the rank order of potencies of the inhibitors mirrored that obtained for the whole-cell assays (both cAMP and PKA). The observed "high-affinity" conformation of the enzyme was not dependent upon a specific cation or anion. The shift in sensitivity of the rhPDE IVa enzyme for r-rolipram in the presence of increased ionic strength was accompanied by an enhanced capacity of the soluble enzyme preparation to specifically bind [$^3$H](R)-rolipram with high-affinity.

DETAILED DESCRIPTION OF THE INVENTION

Figure 1:
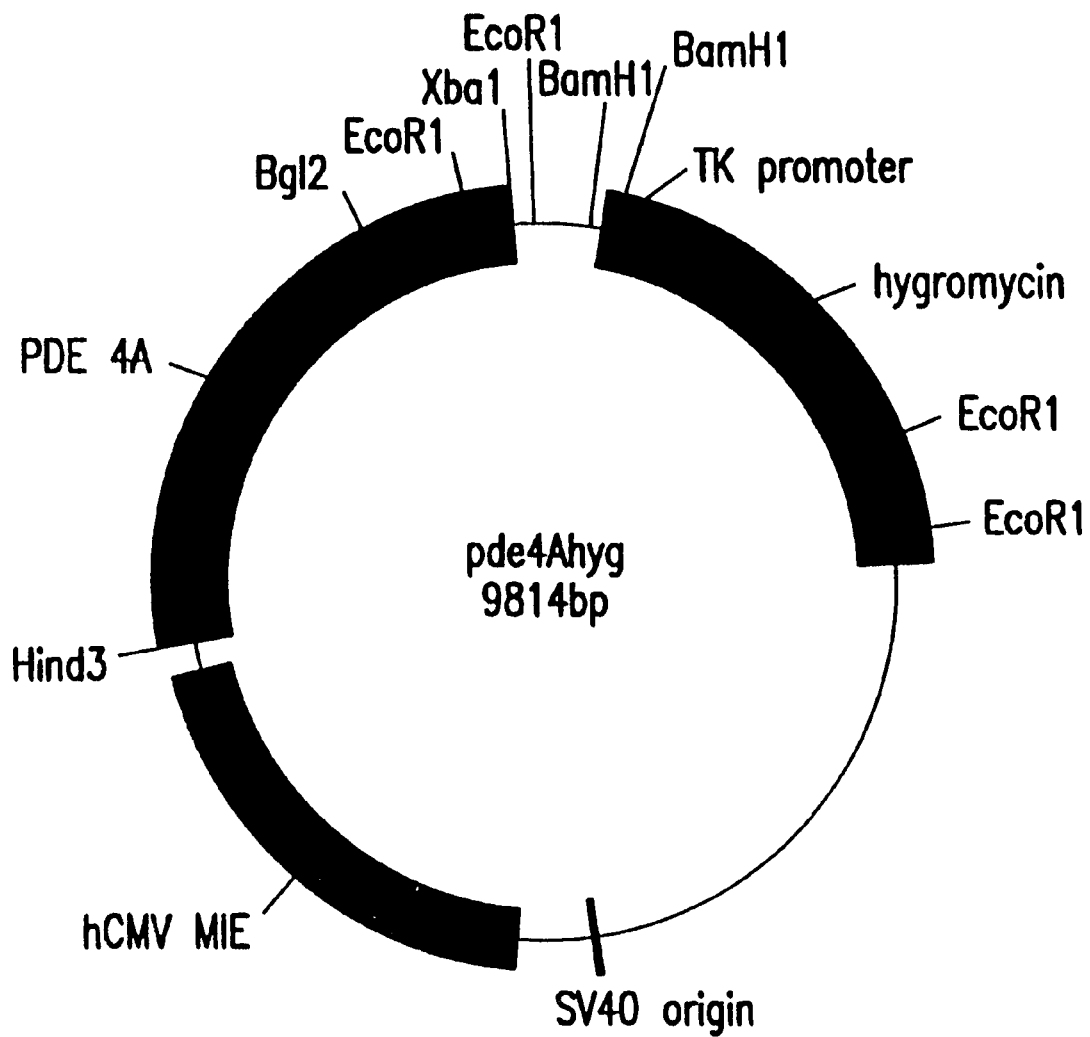
FIG. 1. PDE IVa expression vector

In one aspect the invention encompasses a method of assessing the capacity of an inhibitor of phosphodiesterase IV to inhibit phosphodiesterase IV, comprising the steps of:
  (a) preparing a cell free reaction mixture comprising:
    (1) soluble full length low-Km cAMP phosphodiesterase IVa enzyme;
    (2) test compound; and
    (3) a suitable enhancer of ionic strength;
  (b) incubating said reaction mixture; and
  (c) measuring the phosphodiesterase activity present in said reaction mixture.

For purposes of this specification, the soluble full length low-Km cAMP phosphodiesterase IVa enzyme shall be defined as phosphodiesterase enzyme that has a K$_m$ of 5 μM or less and is at least 100-fold more selective for cAMP as a substrate compared to cGMP. For purposes of this specification., the amount of low-Km cAMP phosphodiesterase IVa used in the method may range from about 0.003 μg/μl to 0.009 μg/μl of CHO-K1 cytosolic extract, preferably about 0.006 μg/μl. [1 μg=1 pmol/min of cAMP hydrolized]

For purposes of this specification., the amount of test compound used in the method may range from about 1 μMol/L to 0.3 nMol/L.

For purposes of this specification the enhancer of ionic strength includes, but is not limited to MgCl$_2$, NaCl, Choline Chloride, NaBr and NaF. For purposes of this specification, the amount of enhancer of ionic strength used in the method may range from 0 mM to about 600 mM, preferably about 300 mM.

For purposes of this specification the incubation period may range from about 5 to 20 min, preferably about 10 min. The temperature of incubation may range from 25 to 37° C., preferably about 30° C.

The means of measuring phosphodiesterase activity, shall include, but is not limited to binding of 5' AMP to Scintillation Proximity Assay Beads, such as manufactured by AMERSHAM,UK.

In a second aspect the invention encompasses a system for stably expressing a soluble low-Km cAMP phosphodiesterase IV enzyme (PDE IV) comprising: CHO-K1 cells transfected with an expression vector for expressing human PDE IV DNA, the expression vector comprising pEE7.

Within this aspect there is a class wherein the system for stably expressing high affinity PDE IV comprises CHO-K1 cells as identified by accession number ATCC CRL 9618, an expression plasmid comprising vector pEE7 and human PDE IV cDNA.

In a third aspect the invention encompasses a method of assessing the capacity of an inhibitor of phosphodiesterase IV to inhibit phosphodiesterase IV, comprising the steps of:
  (a) preparing a reaction mixture comprising:
    (1) CHO-K1 cells stably expressing full length low-Km cAMP phosphodiesterase IVa enzyme;
    (2) prostaglandin I$_2$; and
    (3) test compound;
  (b) incubating said reaction mixture; and
  (c) measuring the phosphodiesterase activity present in said reaction mixture.

For purposes of this specification., the amount of CHO-K1 cells used in the method may range from 0.1 million/ml to 0.4 minllion/ml, preferably about 0.2 million/ml.

For purposes of this specification, the amount of prostaglandin I$_2$ used in the method may range from 5 μMol/L to 20 μMol/L, preferably about 10 μMol/L.

For purposes of this specification, the amount of test compound used in the method may range from 0.0003 μM to 10 μM.

For purposes of this specification the incubation period may range from 5 min to 20 min, preferably about 10 min. The temperature of incubation may range from 20 to 30° C., preferably about 25° C.

The means of measuring phosphodiesterase activity, shall include, but is not limited to determination of cellular cAMP by radioimmune assay.

DETAILED DESCRIPTION OF THE DRAWINGS

FIG. 1. PDE IVa Expression Vector

CHO-K1 cells were transfected with an expression vector containing a 2700 bp cDNA insert encoding for a full-length PDE IVa enzyme as described in Materials and Methods. The expression plasmid is based on the vector pEE7. The following abbreviations are used to describe the features of this plasmid. HCMV MIE: human cytomegalovirus major immediate early gene promoter/enhancer, hyg: hygromycin resistance gene, TK: thymidine kinase, SV40 origin: SV40 origin of replication. The vector also includes an *E.coli* replicon and beta-lactamase gene from the plasmid pBR322.

Figure 2A:
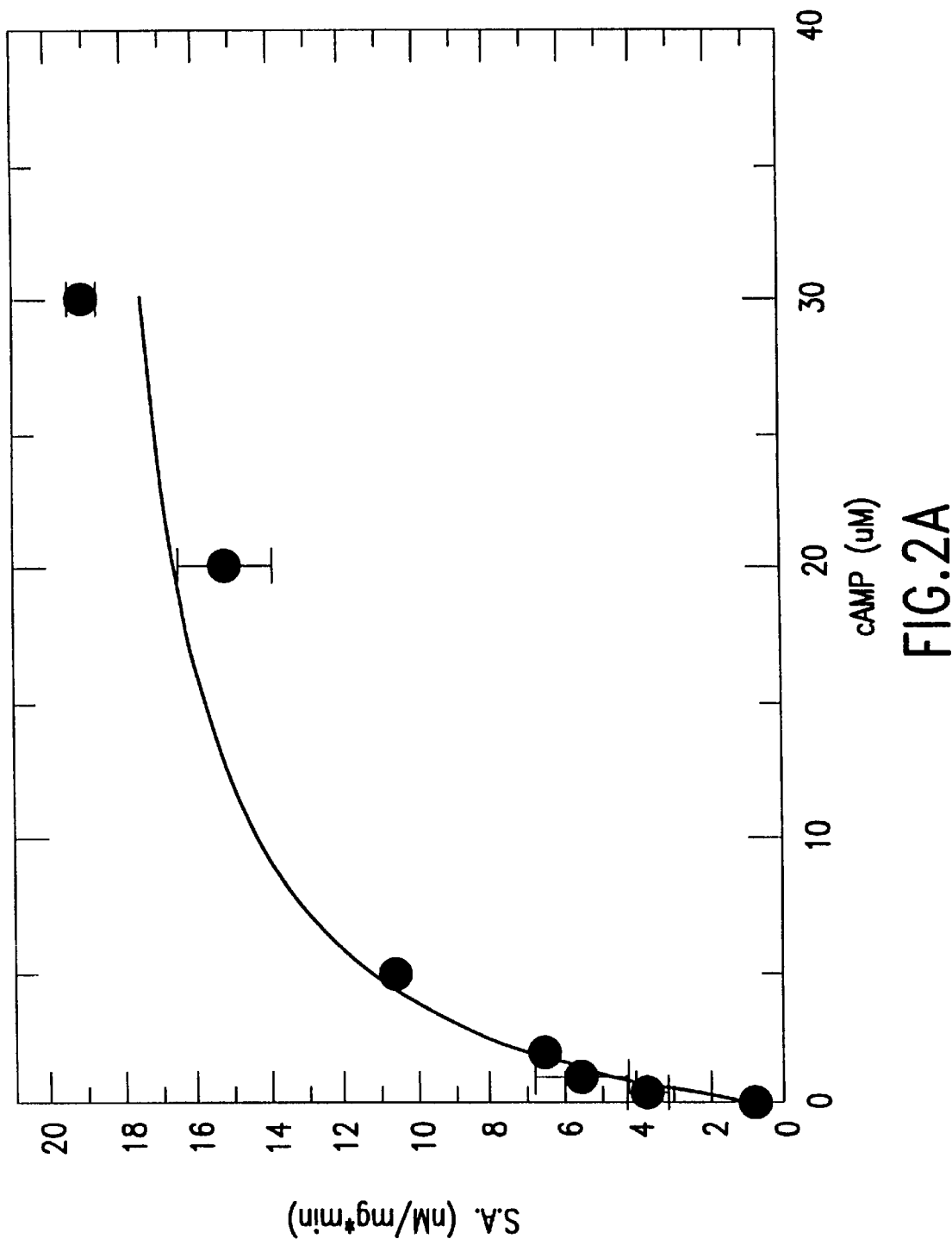
FIG. 2a. Kinetic characteristics of PDE IVa expressed in CHO-K1 cells

FIG. 2a. Kinetic Characteristics of PDE IVa Expressed in CHO-K1 Cells

PDE IVa activity was assayed in the 100,000×g supernatant obtained from sonicated CHO-K1 cells stably expressing the enzyme. The enzyme activity was assayed in duplicate at substrate concentrations ranging from 0.2 $\mu$M to 30 $\mu$M using the Amersham SPA beads as described in Materials and Methods. Shown are the saturation kinetics for the enzyme. The inset graph is a double-reciprocal plot of the kinetic data. Average of 3 separate experiments +/- SD.

Figure 2B:
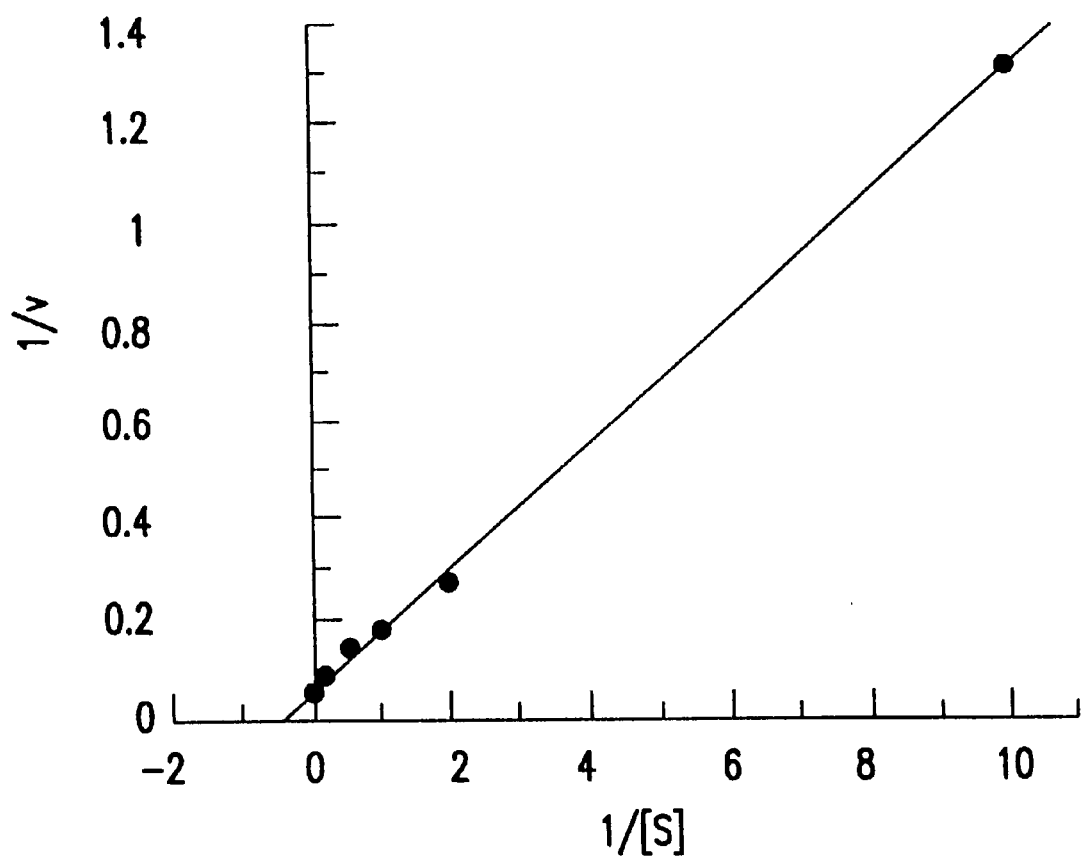
FIG. 2b. Kinetic characterization of HSPDE4A4B expressed in CHO-K1 cells

FIG. 2b. Kinetic Characterization of HSPDE4A4B Expressed in CHO-K1 Cells.

Panel A. Shown are the saturation kinetics for the enzyme.PDE IVA activity was assayed in the 100,000×g supernatant obtained from sonicated CHO-K1 cells stably expressing the enzyme. The enzyme activity was assayed in duplicate at substrate concentrations ranging from 0.2 mM to 10 mM using the Amersham SPA beads as described in Materials and Methods. Average of 3 separate experiments +/- SEM. Panel B. Double-reciprocal replot of the averaged saturation data.

Filled circles represent enzyme activity measured as described in Materials and Methods. Filled squares are data obtained in the presence of 300 mM KCl.

Figure 3A:
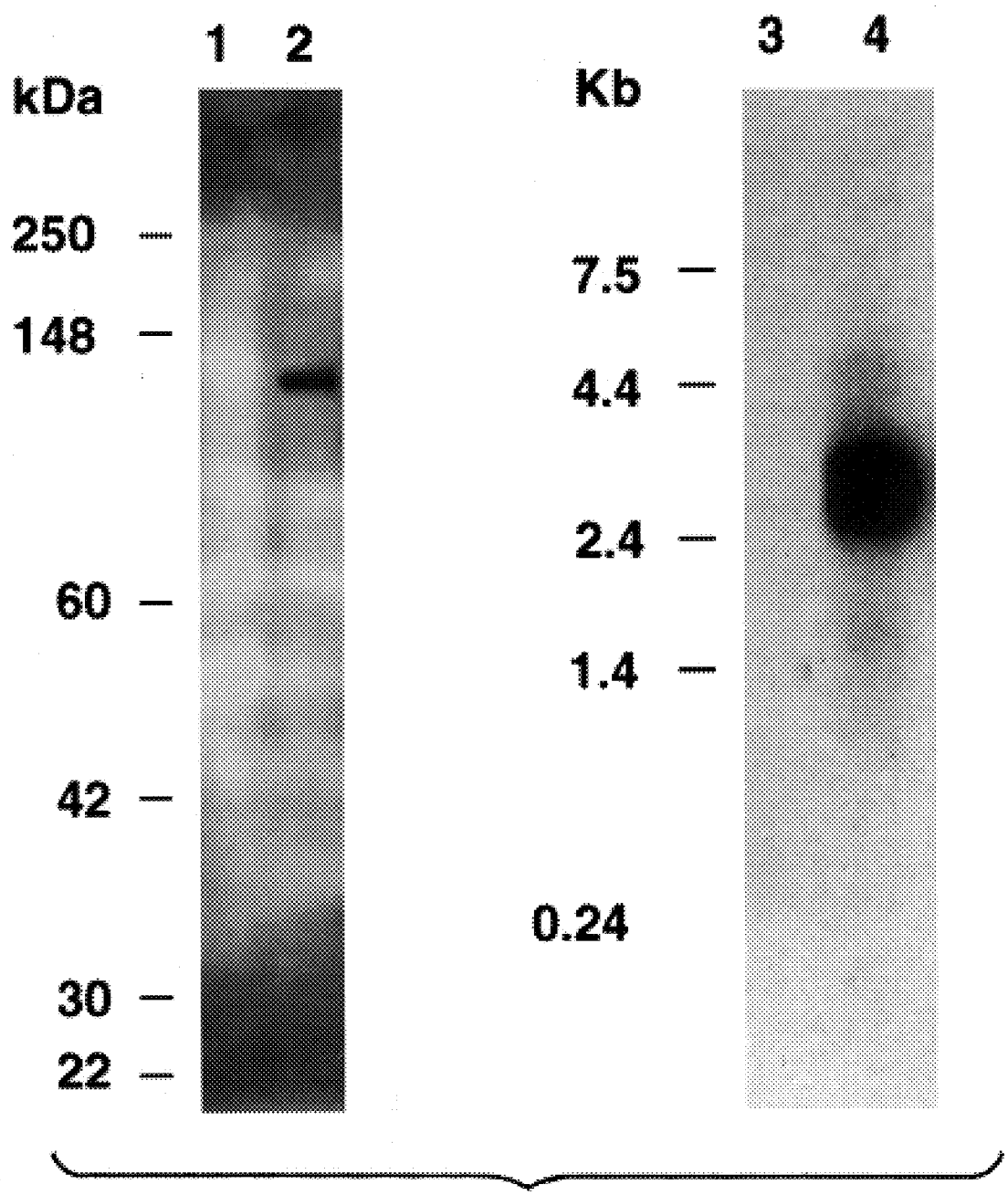
FIG. 3a. Detection of mRNA transcripts encoding for full-length PDE IVa and expression of protein in transfected CHO-K1 cells FIG. 3b. Immunocytochemistry of transfected CHO-K1

FIG. 3a. Detection of mRNA Transcripts Encoding for Full-Length PDE IVa and Expression of Protein in Transfected CHO-K1 Cells Panel A. Western blot analysis for PDE IVa enzyme expression was performed on the soluble portion of CHO-K1 cells transfected with a vector missing the PDE IVa CDNA insert (Lane 1) and CHO-K1 cells expressing high PDE IV activity (Lane 2). The blot was probed with a rabbit anti-PDE IVa antibody raised against the C-terminus of the enzyme. Panel B. Northern blot analysis for PDE IVa mRNA transcripts. Poly-A RNA was extracted from control CHO-K1 cells grown in hygromycin B selection media (Lane 3) and clones stably expressing PDE IV activity (Lane 4). The blot was probed with a 32P-labelled 420 bp oligonucleotide obtained by PCR amplification of a stretch of PDE IVa cDNA from nucleotide 2392 to 2859. The blot was washed with 2×SSC containing 0.1% SDS.

Figure 3B:
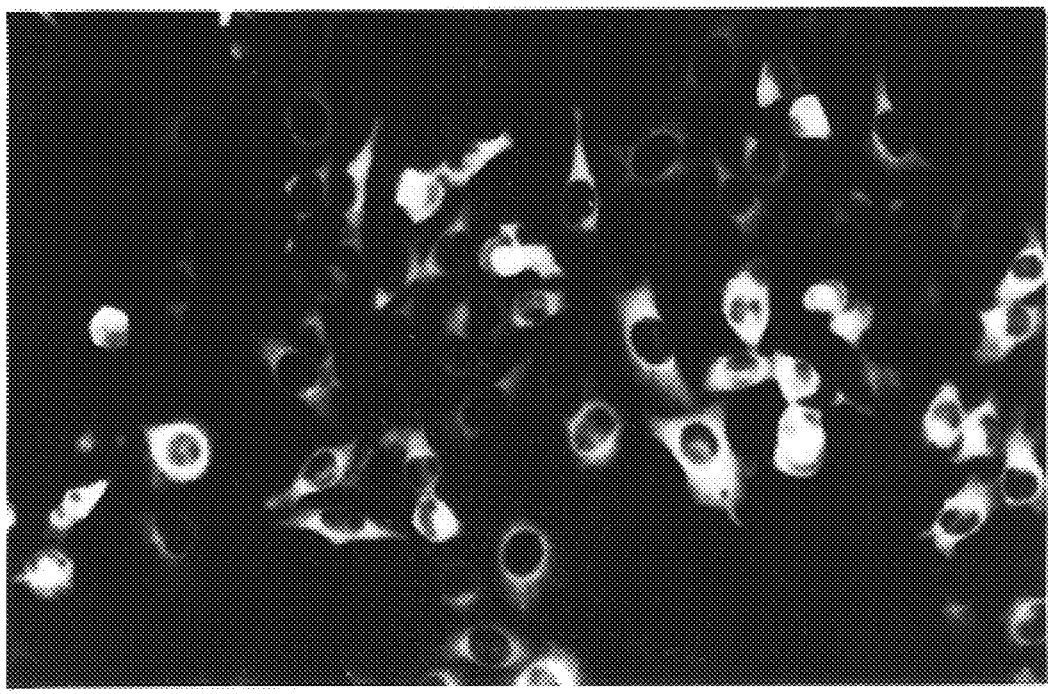
Figure 3B:
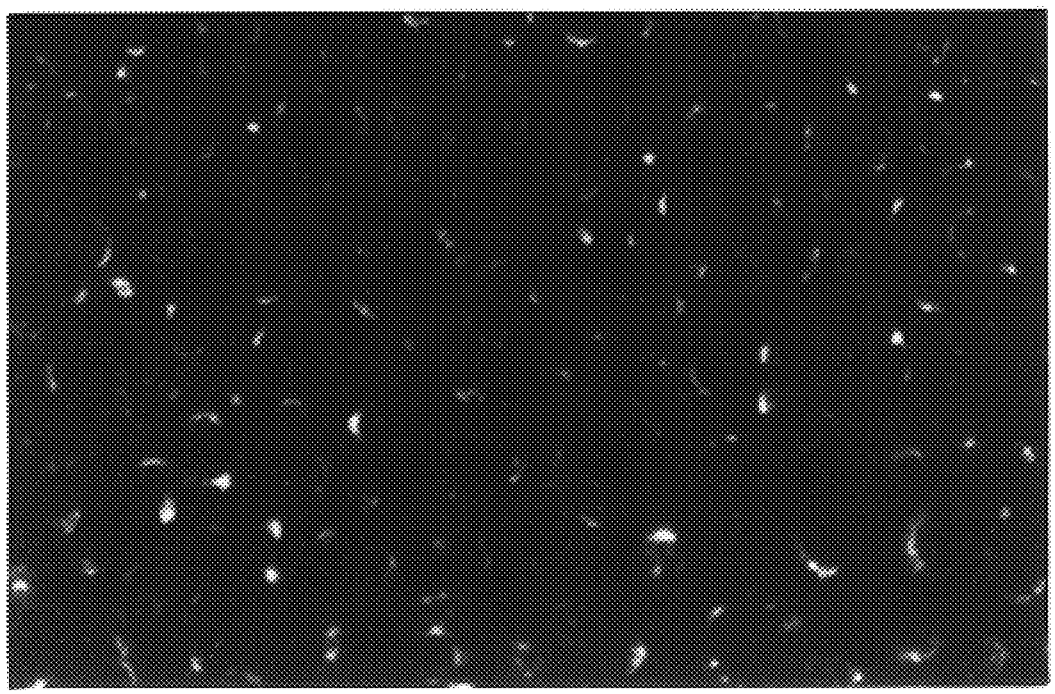

FIG. 3b. Immunocytochemistry of Transfected CHO-K1

Immunocytochemistry. CHO-K1 cells transfected with either the pEE7 expression either containing (panel A) or not containing (panel B) the cDNA insert encoding for HSPDE4A4B were grown. under both hygromycin B and G418 selection. The cells were fixed with an ice cold solution of 100% methanol for 10 minutes on ice. Rabbit antisera raised against the NH2-terminus of HSPDE4A4B was diluted 1/500 and incubated at 40° C. overnight. The cells were washed with 3 changes of PBS. A donkey anti-rabbit secondary antibody conjugated to $C_y3$ (indocarbocyanine) was incubated with the cells. The labeled cells were rinsed and visualized with an Olympus fluorescence microscope. Similar data were obtained using an antisera raised against an epitope contained within the catalytic domain of the enzyme.

Figure 4:
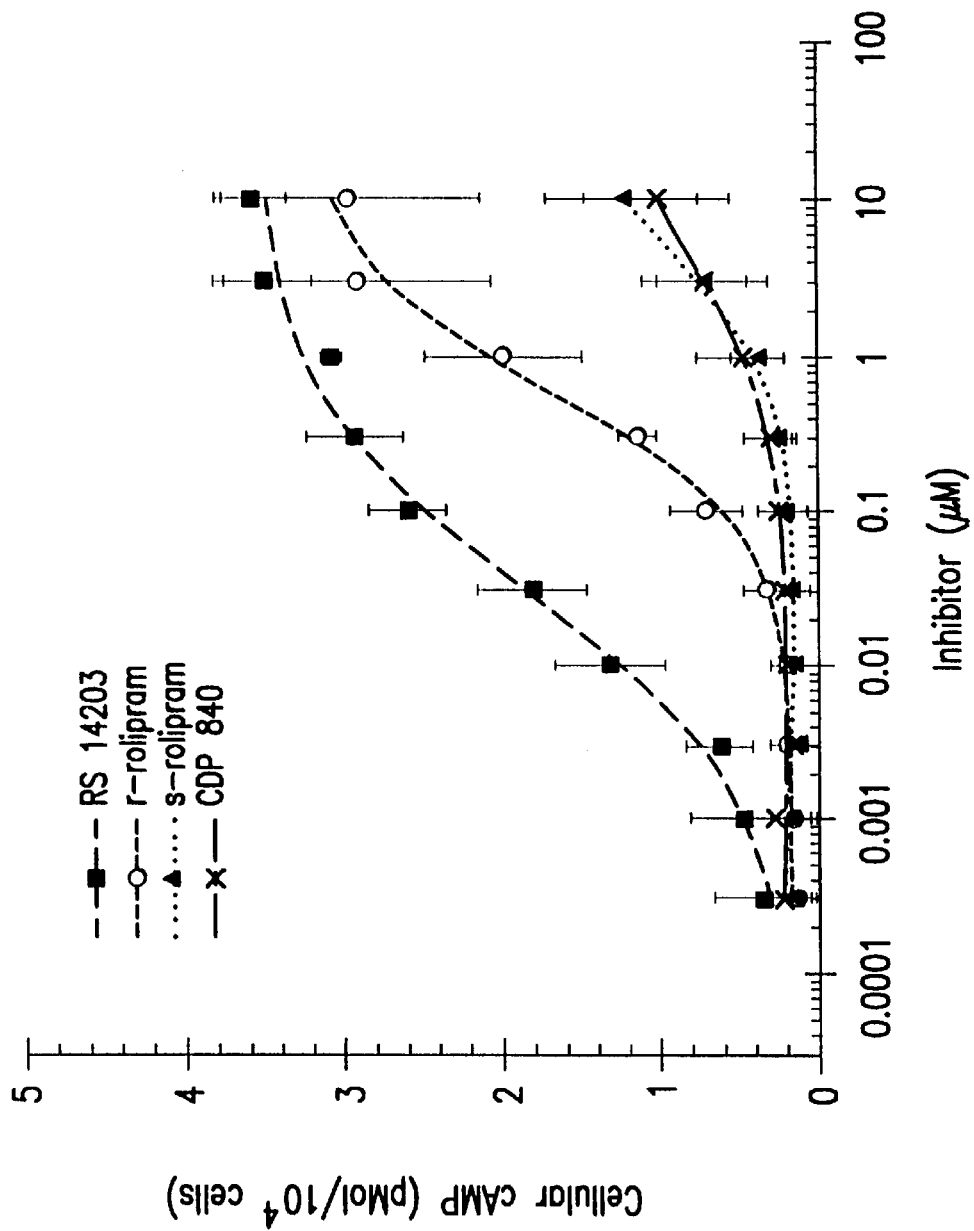
FIG. 4. Effect of selective PDE IV inhibitors on cAMP accumulation in CHO-K1 cells expressing recombinant human PDE IV enzyme (rhPDEIVA)

FIG. 4. Effect of Selective PDE IV Inhibitors on cAMP Accumulation in CHO-K1 Cells Expressing Recombinant Human PDE IV Enzyme (rhPDEIVA)

Levels of cAMP were measured in CHO-K1 cells stably expressing PDE IVa enzyme as outlined in Materials and Methods. The effect of PDE IV selective inhibitors was examined in the presence of 10 $\mu$M $PGI_2$. $PGI_2$ alone increased basal cAMP content 2-fold. Shown is the mean of 3 experiments±SD.

Figure 5:
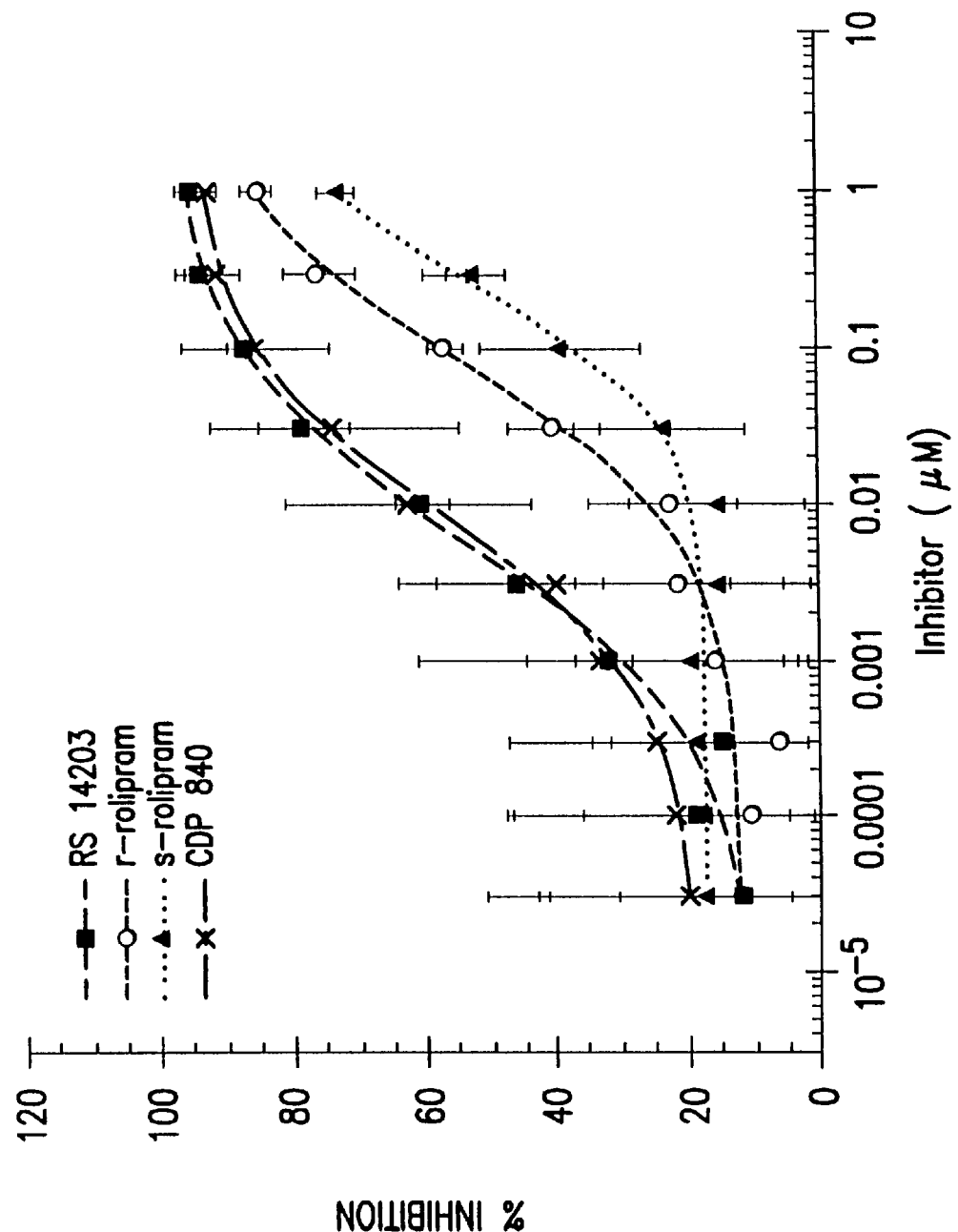
FIG. 5. Inhibition of human recombinant PDE IVa activity in CHOK1 cells by PDE IV specific compounds FIG. 6. Effect of PDE IV inhibitors on whole-cell PKA activity FIG. 7. Effect of MgCl$_2$ on PDE IV inhibitor potencies FIG. 8. Cation and anion dependence of high-affinity rolipram PDE IVa enzyme state FIG. 9. Comparison of PDE IV inhibitor rank potency and cAMP elevation in CHO-K1 cells stably expressing rhPDE IVa enzyme.

FIG. 5. Inhibition of Human Recombinant PDE IVa Activity in CHO-K1 Cells by PDE IV Specific Compounds Inhibition of soluble rhPDEIVa by specific inhibitors was examined at 100 nM substrate. Enzyme activity was determined as described in Materials and Methods using the Amersham SPA beads that specifically bind 5'AMP. Shown is the mean of 3 experiments±SD.

Figure 6:
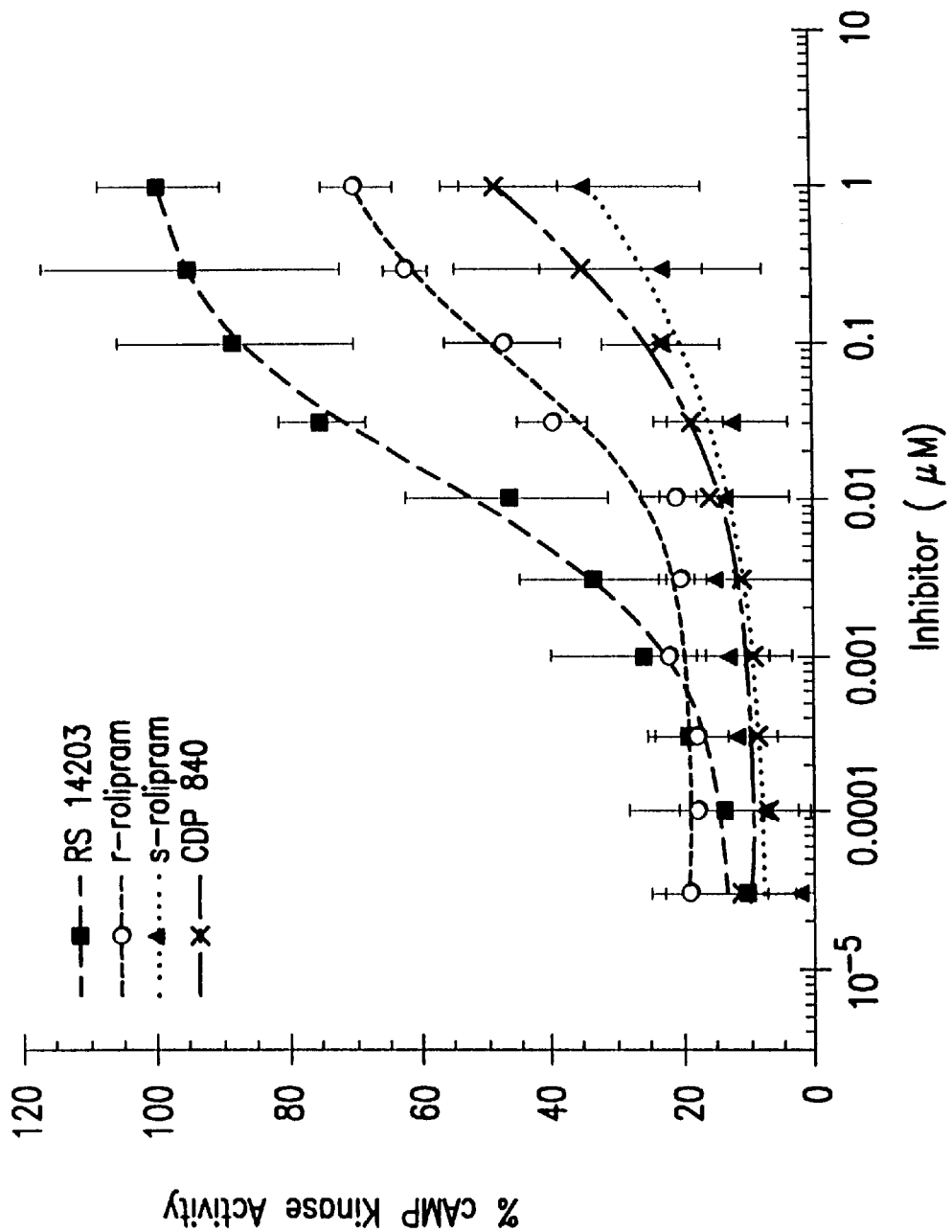
Figure 7A:
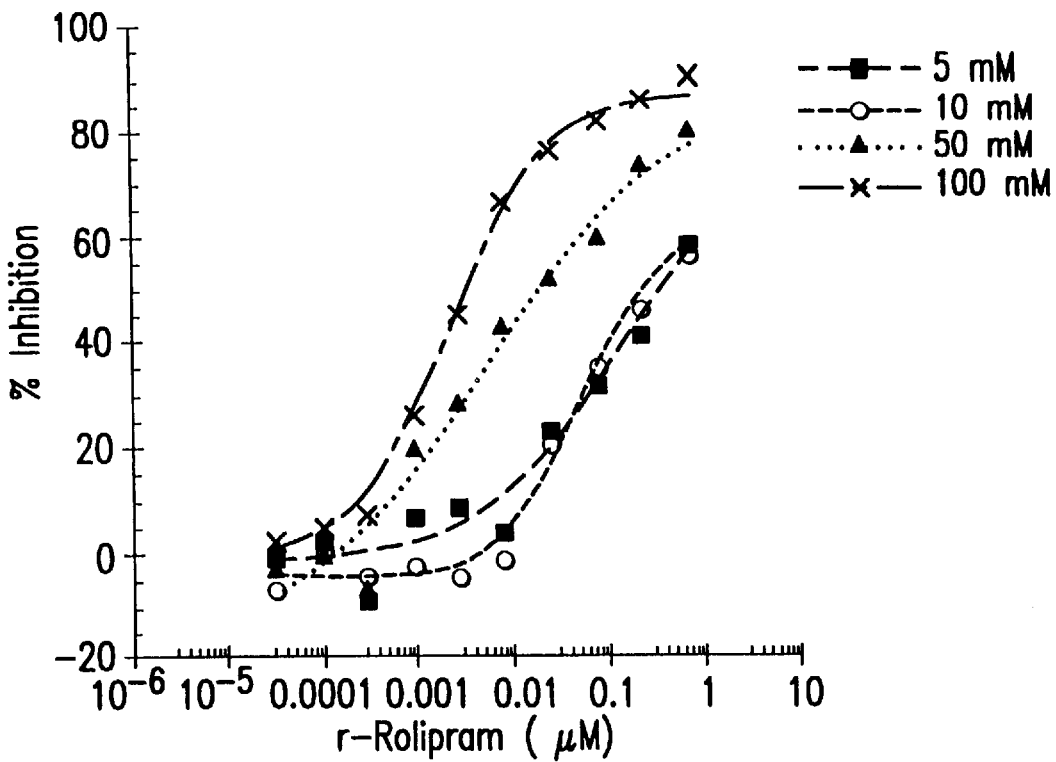
Figure 7B:
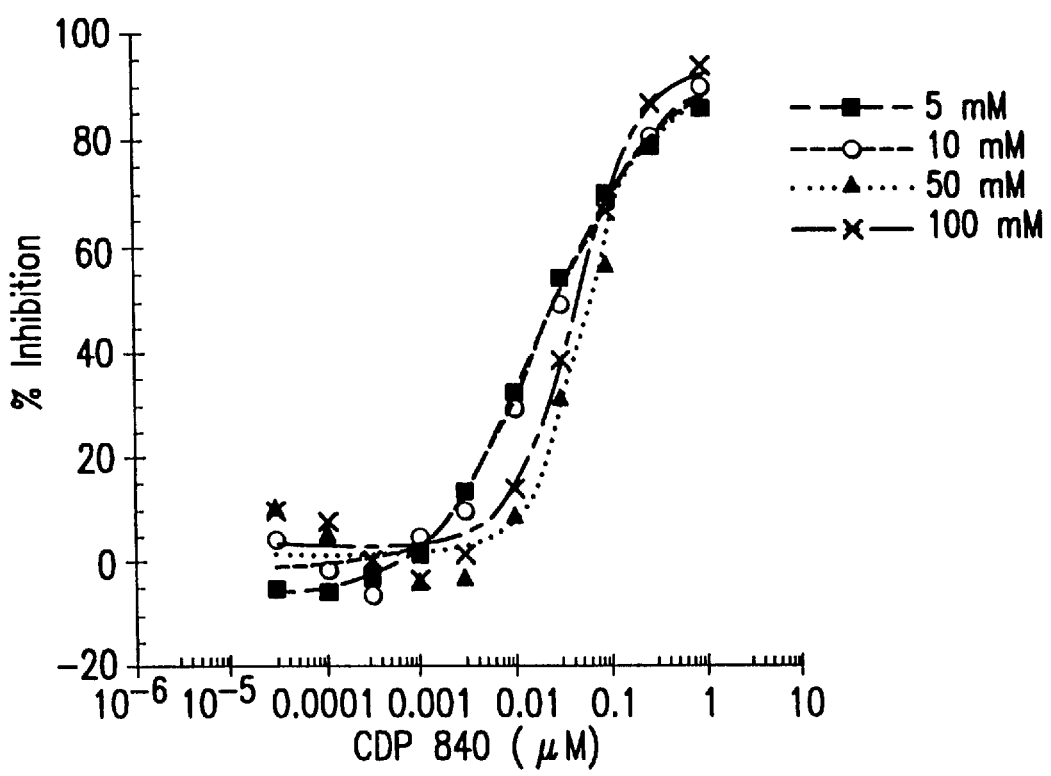
Figure 7C:
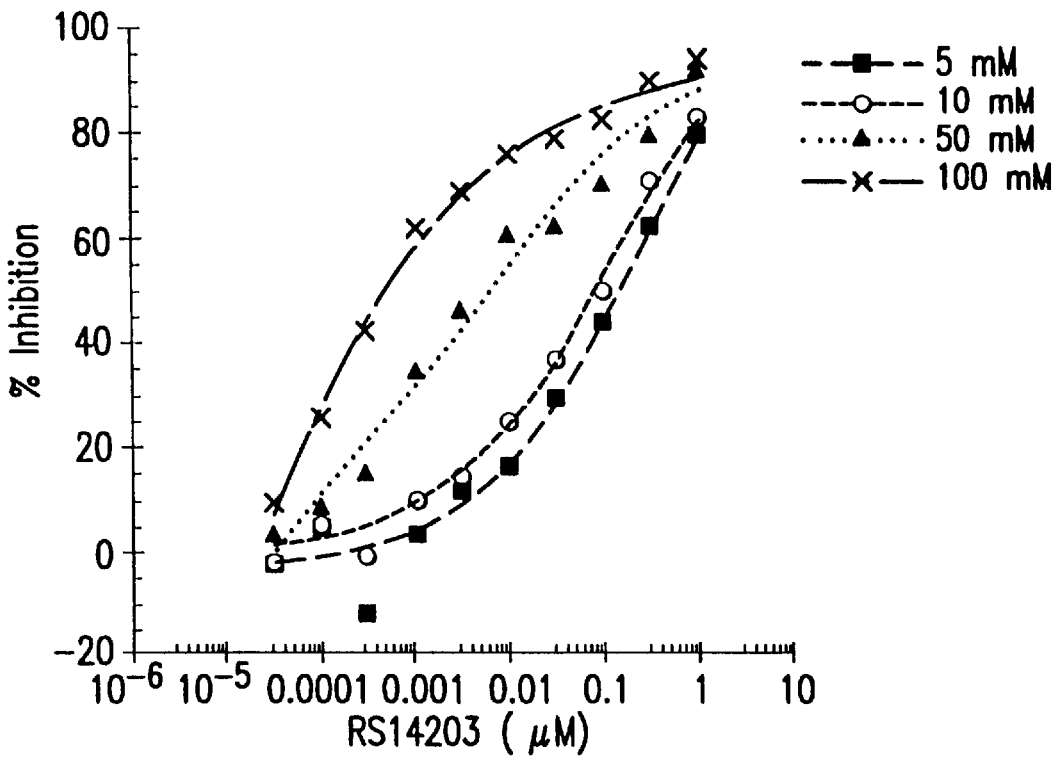
Figure 7D:
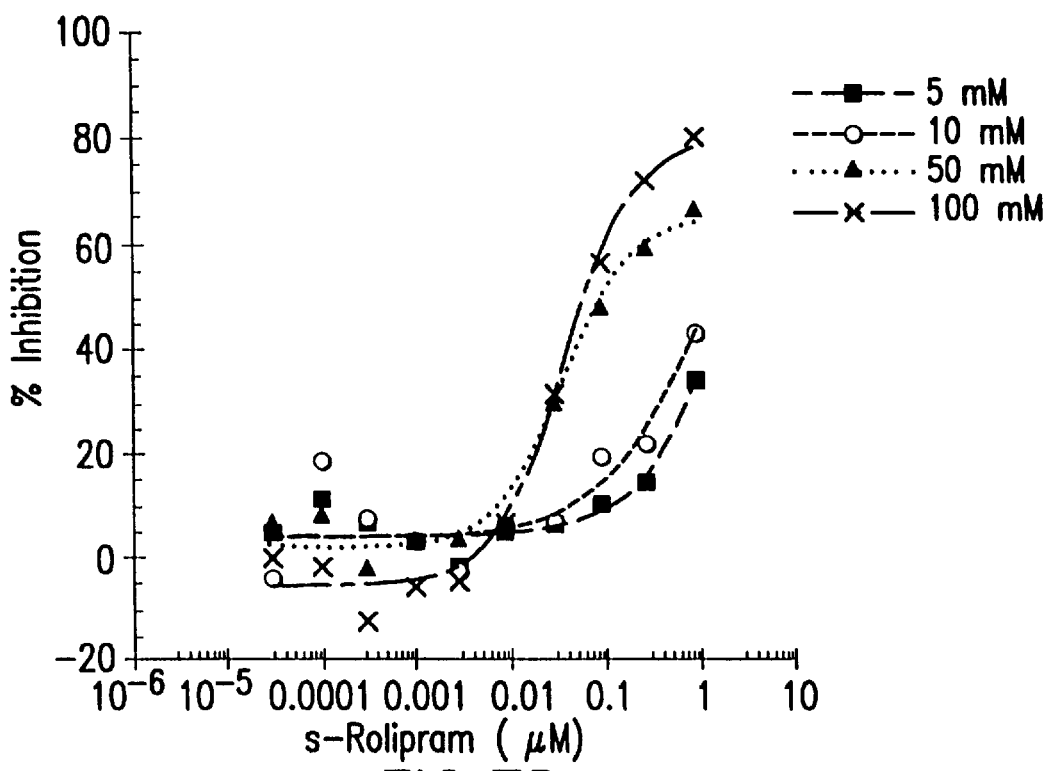

FIG. 6. Effect of PDE IV Inhibitors on Whole-Cell PKA Activity

The effect of PDE IV inhibitors on whole-cell PKA activity was examined in the presence of 1 $\mu$M $PGI_2$. PKA activity ratios were determined as the amount of $^{32}P$ transferred to histone F2B in the presence and absence of cAMP as described in Materials and Methods. Data points represent the fractional PKA activation by incubating cells with the indicated concentrations of inhibitor and 1 mM $PGI_2$. Experiments were performed in triplicate. n=3 experiments±SD.

FIG. 7. Effect of $MgCl_2$ on PDE IV Inhibitor Potencies

Inhibition of soluble rhPDEIVa by specific inhibitors was examined in the presence of 5 mM to 100 mM $MgCl_2$. Enzyme activity was determined as described in Materials and Methods using the Amersham SPA beads that specifically bind 5'AMP in the presence of 10 mM cAMP substrate.

Figure 8A:
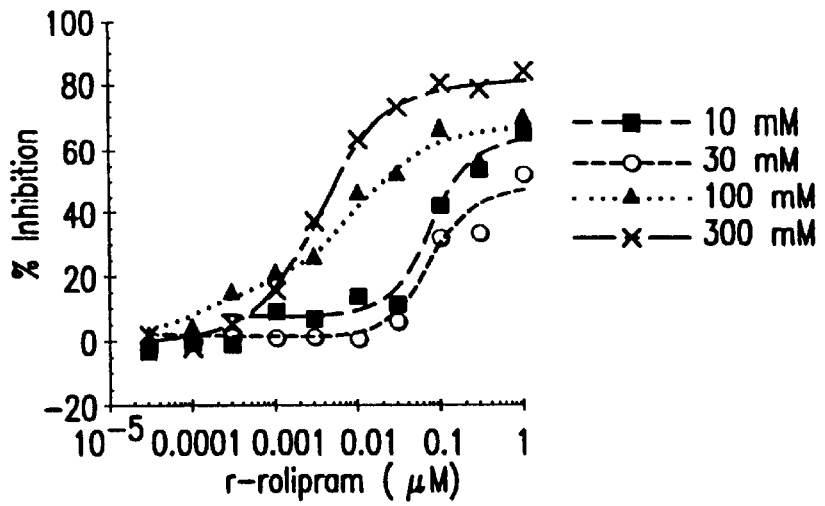
Figure 8B:
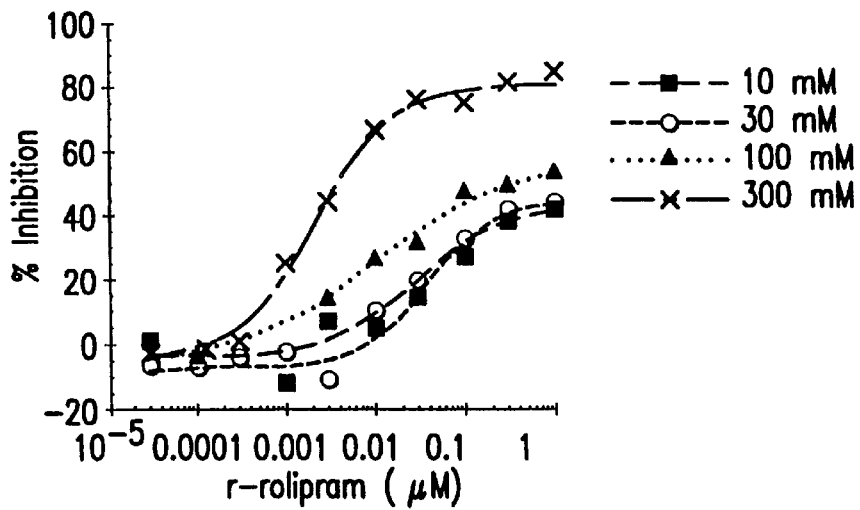
Figure 8C:
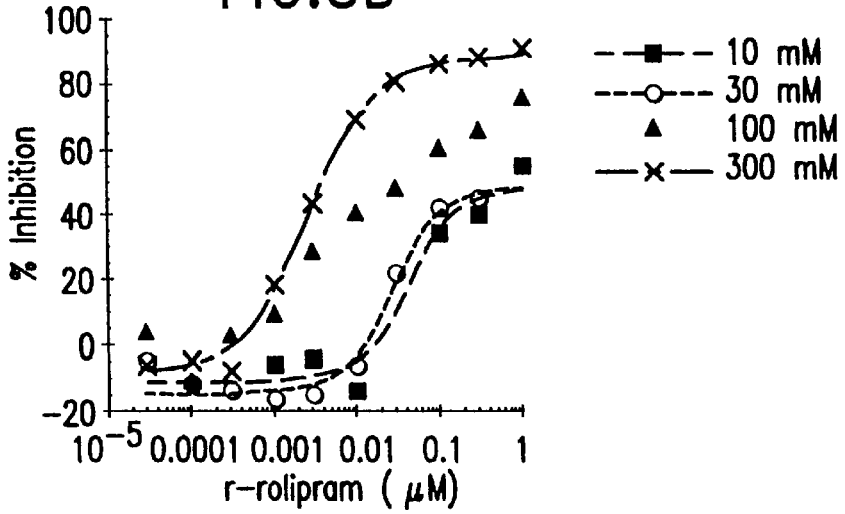

FIG. 8. Cation and Anion Dependence of High-Affinity Rolipram PDE IVa Enzyme State The effects of of increasing choline chloride, KCl, and NaBr concentrations in the PDE IV assay buffer on (R)-rolipram inhibitory potency are shown. Enzyme activity was determined in in a solution containing 50 mM Tris, 10 mM $MgCl_2$, 1 mM EDTA, 10 $\mu$M cAMP, and the indicated amounts of (R)-rolipram and salts.

Figure 9A:
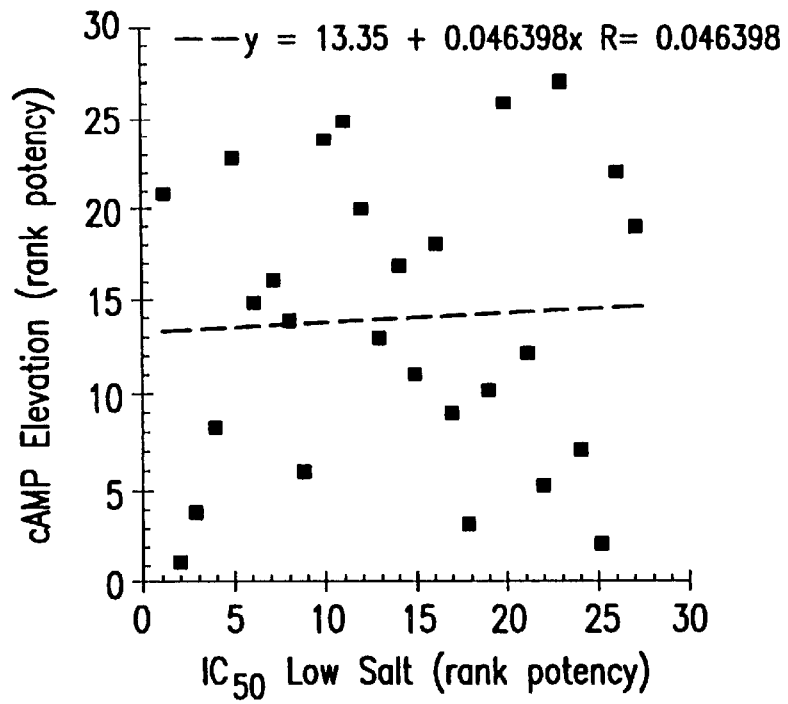
Figure 9B:
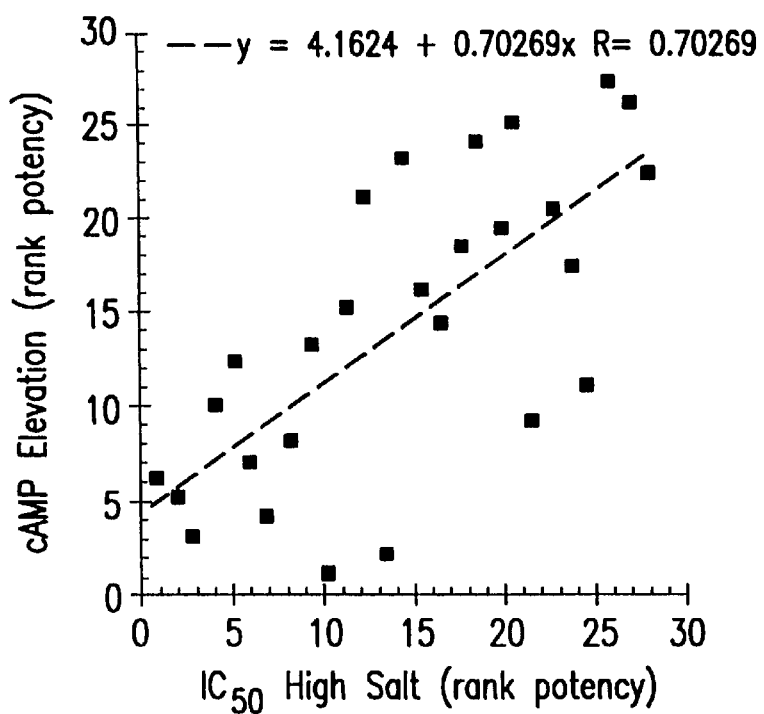

FIG. 9. Comparison of PDE IV Inhibitor Rank Potency and cAMP Elevation in CHO-K1 Cells Stably Expressing rhPDE IVa Enzyme.

The abilities of 27 structurally diverse PDE IV inhibitors to elevate cAMP in CHO-K1 cells transfected with cDNA encoding for the full-length rhPDE IVa enzyme was compared to their potencies against the recombinant enzyme determined at either 10 mM (panel A) or 100 mM $MgCl_2$ (panel B).

Figure 10A:
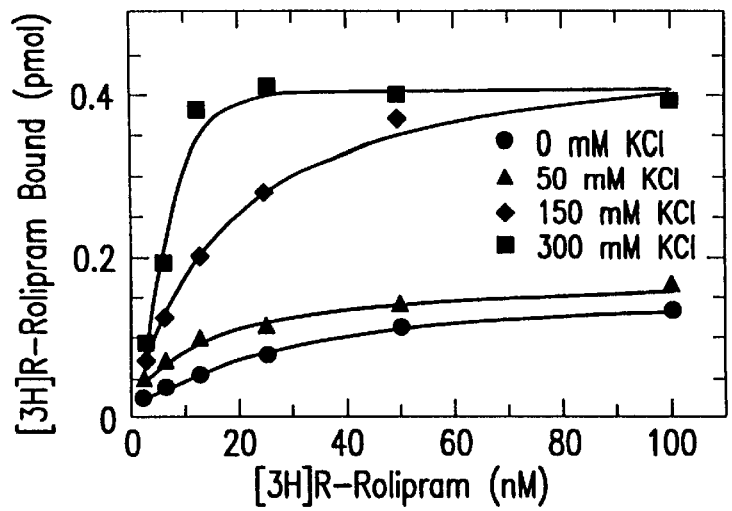
FIG. 10a–c. Effect of ionic strength on [3H](R)-rolipram binding to rhPDE IVa.
Figure 10B:
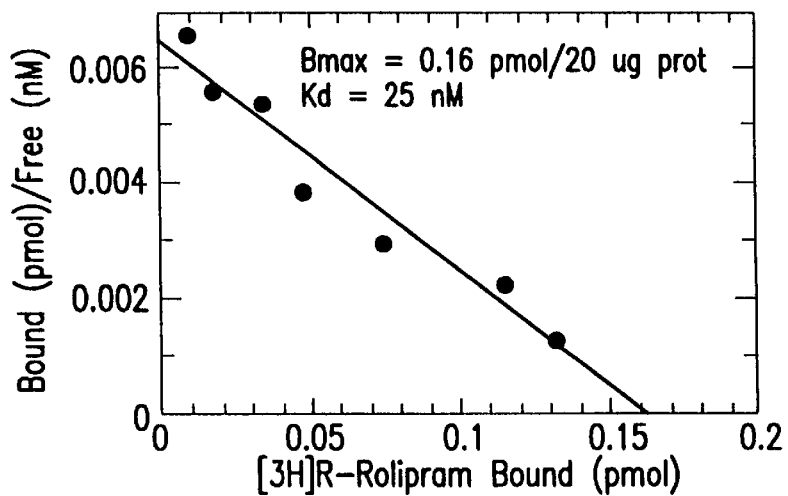
Figure 10C:
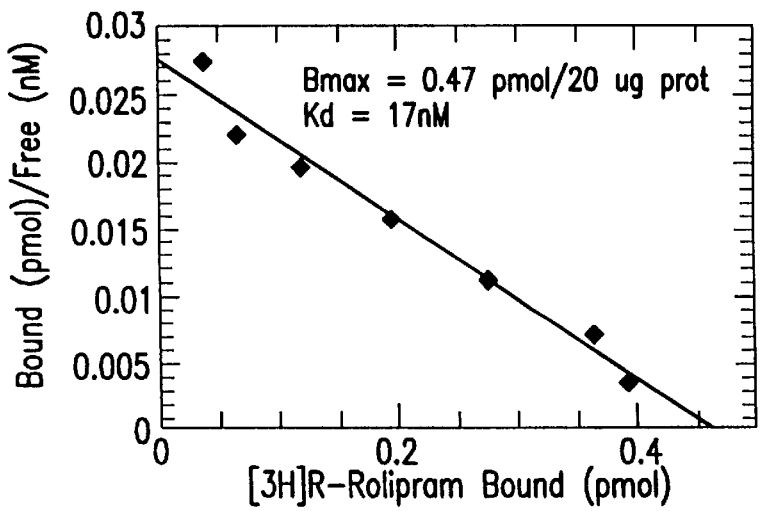

FIG. 10a–c. Effect of Ionic Strength on $[^3H](R)$-Rolipram Binding to rhPDE IVa.

Binding of $[^3H](R)$-rolipram to rhPDE IVa enzyme was examined in the presence of the indicated concentrations of KCl. Shown is the saturable binding to the soluble rhPDE IVa enzyme with increasing concentrations of ligand from 0.2 to 100 nM (panal A). Scatchard analyses of specific $[^3H](R)$-rolipram binding in the presence of 0 mM KCl (panal B) and 150 mM KCl (panal C). Materials and Methods FIG. 10d–e. Effect of KCl and HSA on $[^3H](R)$-Rolipram Binding to FLAG PDE IVA Enzyme.

Binding of [3H](R)-rolipram to purified FLAG PDE IVA enzyme was examined in the presence of the indicated concentrations of KCl and/or 3 mg/ml HSA. Shown is the specific saturable binding to the purified FLAG enzyme with increasing concentrations of ligand from 0.2 to 100 nM (panel A). Each point represents the mean of 3 separate experiments performed in duplicate±SEM. Scatchard analyses of specific $[^3H]$ (R)-rolipram binding in the presence of 0 mM KCl (panel B) and 150 mM KCl+3 mg/ml HSA (panel C). Each point represents the average of 3 separate experiments.

Figure 11:
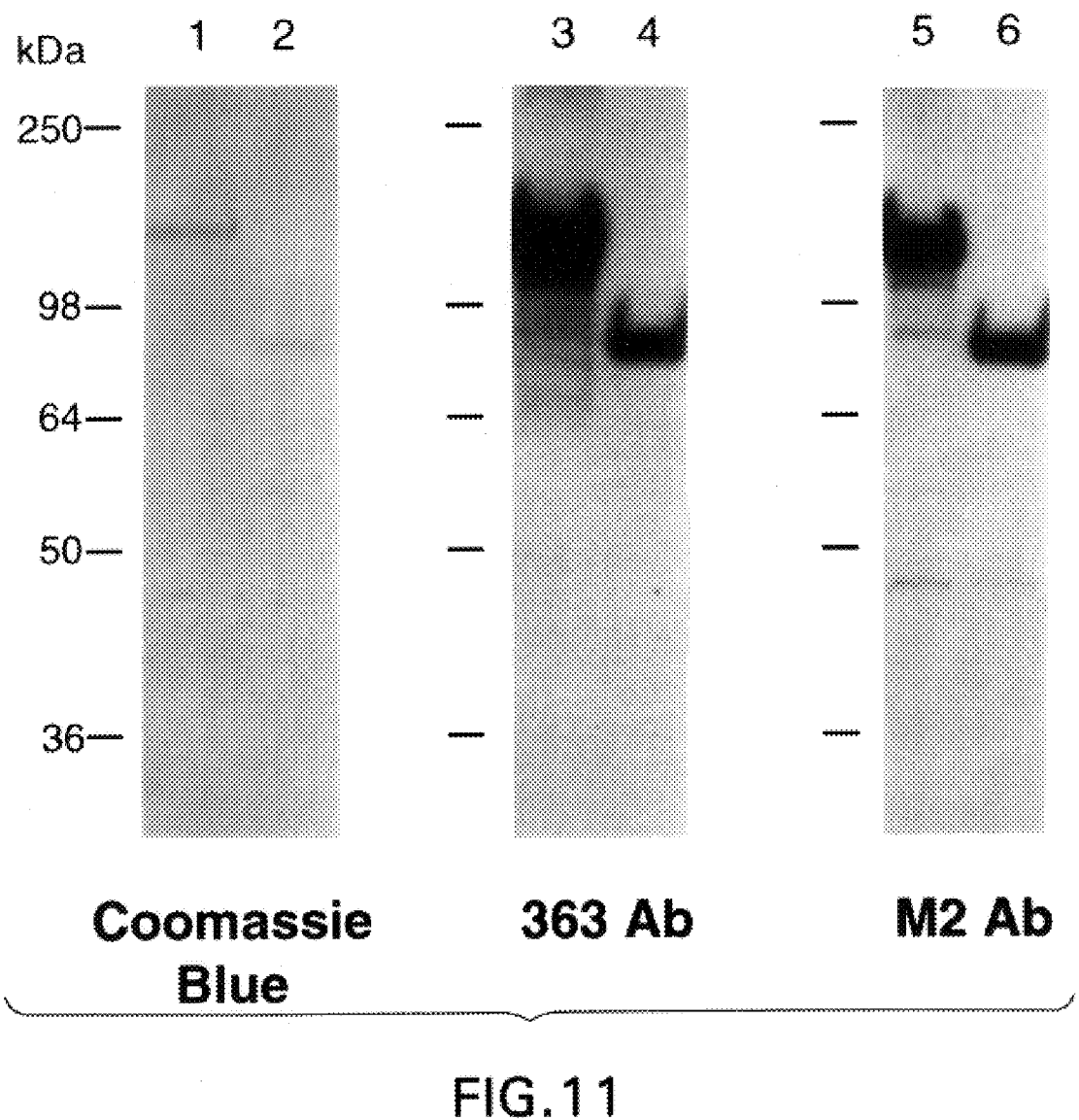
FIG. 11. Purification of FLAG PDE IVA and FLAG PDE IVWA$_{met330}$ enzymes.

FIG. 11. Purification of FLAG PDE IVA and FLAG PDE $IVA_{met330}$ Enzymes.

SDS-PAGE (panel A) and Western blot analysis (panels B and C) was performed on FLAG enzymes eluted from the M2 affinity column as described in Materials and Methods. 3 mg of either FLAG PDE IVA (lanes 1, 3 and 5) or FLAG PDE $IVA_{met330}$ (lanes 2, 4 and 6) were subjected to SDS-PAGE on 4–12% Tris-glycine gels and stained with Commassie Blue (panel A) or transferred onto nitrocellulose membrane and probed with either a rabbit antisera raised against an epitope contained within the catalytic domain of PDE IVA (panel B) or a murine anti-FLAG monoclonal antibody (panel c).

Figure 12A:
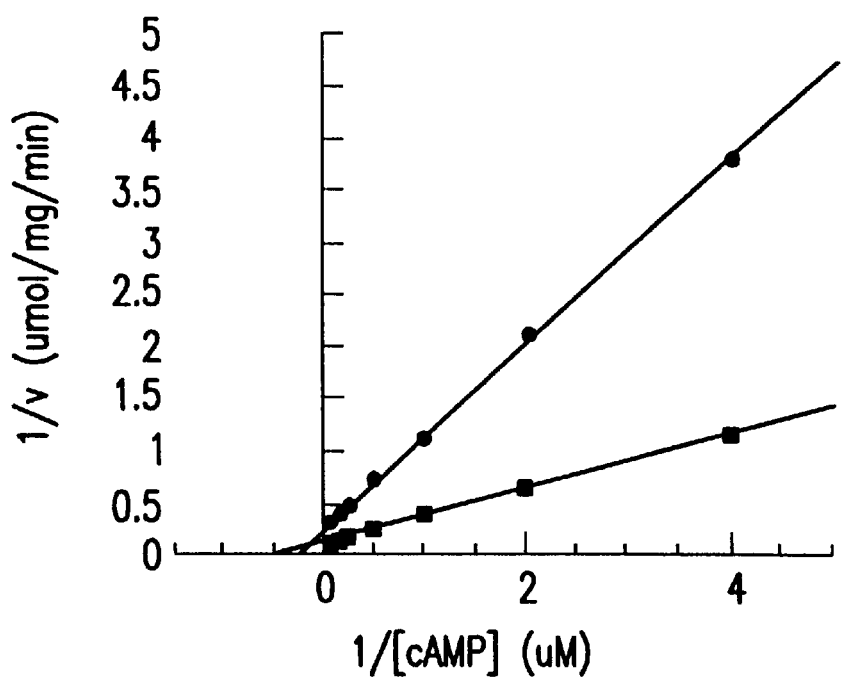
FIG. 12. Kinetic characterization of FLAG PDE IVA and FLAG PDE IVA$_{met330}$ enzymes.
Figure 12B:
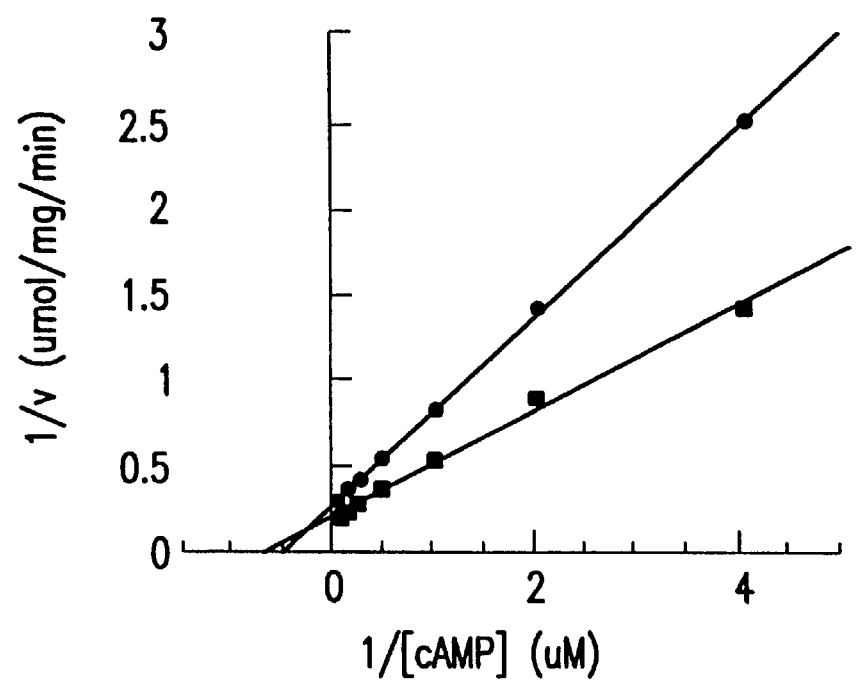

FIG. 12. Kinetic Characterization of FLAG PDE IVA and FLAG PDE IVAmet$_{330}$ Enzymes.

Shown are the double reciprocal plots of the FLAG PDE IVA (panel A) and FLAG PDE IVA$_{met330}$ (panel B) enzyme activities with respect to cAMP measured in the presence of 150 mM KCl (filled squares) or 150 mM KCl/3 mg/ml HSA (filled circles). Each point represents the mean of 3 separate experiments performed in duplicate ±SEM.

FIG. 13. Effect of KCl and HSA on FLAG PDE IVA and FLAG PDE IVA$_{met330}$ Sensitivity to (R)-Rolipram Inhibition.

FLAG PDE IVA (panel A) and FLAG PDE IVA$_{met330}$ (panel B) were assayed under the indicated conditions as described in Materials and Methods in the presence of increasing concentrations of (R)-rolipram. Shown are the averages of 3 separate experiments±SEM.

Compounds Evaluated Include the Following:

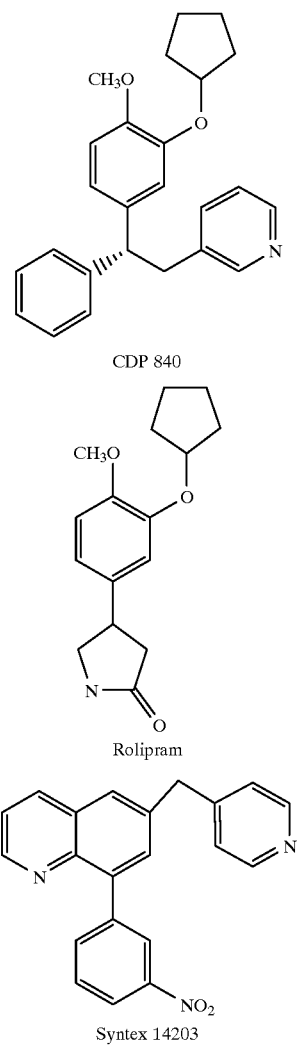

CDP 840

Rolipram

Syntex 14203

Cloning of Full-Length cDNA for the PDE IVa Enzyme

A human PDE IVa cDNA was obtained from a human frontal cortex cDNA library (CLONETECH) by hybridization with a partial cDNA isolated from the human monocytic cell line U937 (23). With the exception of a methionine to isoleucine change at residue 724, the translated amino acid sequence of this cDNA was identical to that reported by Bolger et al (30).

Generation of Anti-PDEIVa Antisera

A rabbit polyclonal antiserum was raised to a fusion protein comprised of glutathione-S transferase linked to the carboxyl terminal 162 amino acids of human PDE IVa.

Establishment of CHO-K1 Cell Lines Stably Expressing PDE IVa Enzyme

CHO-K1 cells stably expressing the prostacyclin receptor and grown under G418 selection as described previously (20) were plated at a density of 1.75×106 cells/175 cm$^2$ in a T-175 flask (Gibco, Burlington, Vt.) containing alpha MEM media; 10% heat inactivated fetal bovine serum (FBS); 1% (v/v) penicillin/streptomycin; 25 mM Hepes, pH 7.4; and 500 μg/ml G418 (complete media). The cells were placed in an incubator for 24 hr at 37° C. and 5% $CO_2$. The cells were then washed with warmed sterile phosphate buffered saline (PBS) and incubated with 2 μg/ml DNA, and 9 μg/ml lipofectamine reagent in Opti-MEM for 7 hr at 37° C. and 5% $CO_2$. The incubation solution was diluted 1:2 with Opti-MEM containing 20% FBS and incubated overnight. Following the overnight incubation, the media was replaced by complete media containing 500 μg/ml hygromycin B. Colonies were identified and grown in T-175 flasks for further characterization.

Measurement of Whole-Cell cAMP Content

CHO-K1 cells were plated at a density of 10$^6$ cells/175 cm$^2$ containing complete media with 500 μg/ml hygromycin. The flasks were maintained in an incubator at 37° C. with 5.0% $CO_2$ for 72 hr. The media was changed and the cells were allowed to grow overnight. The cells were washed and dissociated from the plate with PBS containing 0.5 mM EDTA. Cellular cAMP content was measured by centrifuging the cell suspension at 150 g×10 min and resuspending the cells in a Hanks buffered salt solution at a density of 0.2×10$^6$ cells/ml. The cells were preincubated at room temperature for 15 min and then incubated with 10 μM prostaglandin $I_2$ ($PGI_2$) and the indicated compound for an additional 10 min. Basal cAMP levels were determined by incubating the cells in 0.1% DMSO. The incubations were terminated by the addition of HCl (0.1N final) and the cells measured for cAMP.

Determinations of whole-cell cAMP content were performed by incubating 100 μl reconstituted rabbit anti-succinyl cAMP serum with 100 μl of the whole-cell reaction or known cAMP standard and 30 pmol of 125I-cAMP TME in a SCINTISTRIP™ well (300 μl final volume) at room temperature for 18 h. Total cpm (Bo) was determined in the absence of sample or cAMP standard. The reaction mixture was then aspirated out of the well, and individual wells were counted in a BECKMAN LS 6000SC with the window open from 10–999 for 1 min. The data were expressed as %B/Bo= [(standard or sample cpm—non-specific cpm)/(Bo cpm-non-specific cpm)]×100. Non-specific cpm were determined by incubating only the 125I-cAMP TME with assay buffer (50 mM acetate; pH 5.8) in the ScintiStrip™ well. All determinations were performed in triplicate.

cAMP Dependent Protein Kinase Activity Ratio.

CHO-K1 cells were grown and resuspended as described above except that the Hank's buffer was replaced by a solution containing 0.25M sucrose; 10 mM Tris, pH 7.5; and 0.5 mM EDTA. The cells were preincubated and incubated with 1 μM $PGI_2$ and the indicated compounds at room temperature as described above. The incubations were terminated by the addition of 0.05% Triton X-100 (final) and incubating the cells for 5 min on ice. Protein kinase activity was measured in a medium containing 0.83 mM $^{32}$P ATP (sodium salt); 100 μg histone F2B; 30 mM MgCl$_2$; 1 μM IBMX; 10 mM DTT; and 8 mM PO4 buffer, pH 6.6. This mixture (final volume 220 μl) was incubated in a waterbath for 30 min at 35° C. and terminated by adding 5 ml of ice cold 5% TCA. The precipatated protein was applied to a Whatman GF/B filter under vacuum and the filter was subsequently washed with 3×5 ml ice cold TCA solution. The amount of –32P incorporation was measured by placing the filters in Aquasol and counting in a BECKMAN LSC 5000. Basal cAMP independent protein kinase activity was determined by the inclusion of 1 μM Protein Kinase A Peptide Inhibitor (19) in the reaction mixture. Maximal cAMP protein kinase activity was determined in the presence of 10 μM cAMP. All determinations were performed in triplicate and activity ratios were calculated as the [(kinase activity in the presence of PDE inhibitor minus cAMP independent kinase activity)/(maximal cAMP kinase activity minus cAMP independent kinase activity)]×100.

Phosphodiesterase Scintillation Proximity Assay

CHO-K1 cells were lysed by sonication for 10 secs at a power setting of 50% (BRAUNSONIC Model 2000) in an ice cold solution containing 50 mM Tris, pH 7.5; 1 mM EDTA; and 200 μM mercaptoethanol. The soluble and particulate fractions of the cell were obtained by centrifuging the sonicate for 90 min at 100,000×g at 4° C. PDE activity was measured in a solution containing 50 mM Tris, pH 7.5; 10 mM MgCl$_2$; 1 mM EDTA; and 100 nM (or indicated) 3H-cAMP (100 ml final volume) in the presence of varying concentrations of inhibitor. The reaction mixture containing enzyme was incubated for 10 min at 30° C. in 96-well View Plates (PACKARD), and terminated by the addition of 50 μl Phosphodiesterase Scintillation Proximity Assay (SPA) Beads (AMERSHAM) containing 18 mM ZnSO$_4$. The amount of 3H-cAMP hydrolysis was determined by counting the plates in a WALLAC 1450 μBeta LSC counter.

Purification of Epitope FLAG Enzymes

CHO-K1 cells stably expressing epitope FLAG PDE IV constructs were lysed by sonication for 10 secs at a power setting of 50% (Braunsonic Model 2000) in an ice cold solution containing 50 mM Tris, pH 7.5; 1 mM EDTA; protease inhibitor cocktail (Boehringer, Montreal, QUE). The soluble and particulate fractions of the cell were obtained by centrifuging the sonicate for 90 min at 100,000×g at 40° C. Twenty-five ml. (2 mg prot/ml) of the soluble extract was applied (0.01 mmin) to a Pharmacia C 10 column packed with Anti-FLAG M2 affinity gel (Inter Science, Toronto, ONT) equilibrated in 50 mM Tris-HCl, 150 mM NaCl; pH 7.5, maintained at 4° C. in a refrigerated cabinet. The affinity matrix was washed with column buffer until all unbound protein was eluted from the column as determined with a UV-2 flow cell. Bound material was eluted with column buffer containing 0.5 mg/ml. FLAG peptide at a flow rate of 2 ml/min. The eluted material was monitored for (R)-rolipram-sensitive phosphodiesterase activity and M2 immunoreactivity.

[3H](R)-Rolipram Binding Assay

The binding of [3H](R)-rolipram to the soluble PDE IVa enzyme was performed as previously described (27). Briefly, 20 μg of the CHO-K1 soluble fraction was incubated for 10 min. at 32° C. with 0.2 nM to 100 nM [3H](R)-rolipram, (23 Ci/mmol (Amersham)) in a buffer consisting of 50 mM Tris, 5 mM MgCl$_2$, and 0 mM to 300 mM KCl; pH 7.5. The incubation was terminated by rapid filtration through GF/B filters presoaked in 1% polyethyleneimine (SIGMA) using a TOMTEC HARVESTER 96, Mach II (Orange, Conn.). The filters were quickly washed with an ice-cold solution of 50 mM Tris; pH 7.5. Solid MeltiLex B/HS scintillant (WALLAC) was impregnated into the filtermats, and the amount of [3H](R)-rolipram binding to the soluble protein was quantified with a WALLAC 1205 Betaplate reader. Non-specific [3H](R)rolipram binding was measured as above, but in the presence of 10 μM (R)-rolipram. Non-specific binding amounted to less than 5% of the total measured binding activity.

Western Blot Analysis of PDE IVa Enzyme Expression

Membrane bound or soluble protein was subjected to SDSPAGE with 4–12% precast Tris-glycine gels using a NOVEX slab gel apparatus. Prior to SDS-PAGE, samples were incubated in a buffer containing 2% SDS with 10 mM -mercaptoethanol at 95° C. for 2 min. Samples (2–10 μg) were electrophoresed in the gels using a Laemmli buffer system at 100 V for 2 hr. Immunoprobing of PDE IVa enzyme was performed by transferring proteins to nitrocellulose membrane at 30 V for 12 hr in a SDS-free Towbin buffer using a NOVEX transblot apparatus. The transfer-membranes were blocked with 10% skim milk powder in Tris buffered saline and 0.1% Tween 20 (TBS+T) for 24 hr. The membranes were washed twice in TBS+T and incubated with anti-PDE IVa (1:200 dil) in TBS+T and 1% BSA for 1 hr at room temperature. The membranes were again washed in TBS+T and then incubated with an anti-rabbit IG horseradish linked whole Ab from donkey for 1 hr at room temperature. Excess secondary antibody was washed from the membrane with TBS+T and the immunoconjugates were visualized with the AMERSHAM ECL Western blotting detection reagents.

Immunocytochemistry

CHO-K1 cells transfected with either the pEE7 expression containing or not containing the cDNA insert encoding for HSPDE4A4B were grown. under both hygromycin B and G418 selection . The cells were fixed with an ice cold solution of 100% methanol for 10 minutes on ice. The methanol was removed and the cells were rinsed with 3 changes of PBS. To reduce nonspecific background labeling, the cells were incubated for 10 min in Biogenx Universal Blocking reagent. The cells were again washed with 2 changes of PBS. The antisera was diluted ¹⁄1000 and incubated at 4° C. overnight. The cells were washed with 3 changes of PBS. A donkey anti-rabbit secondary antibody conjugated to C 3 (indocarbocyanine) was incubated with the cells at room temperature for 1 hr. The labeled cells were rinsed and visualized with an Olympus fluorescence microscope.

RESULTS

Establishment of a CHO-K1 Cell Line Stably Expressing PDE IVa Activity

CHO-K1 cells stably expressing the prostaglandin IP receptor (20) were transfected with a vector containing a cDNA insert encoding for a full-length human PDE IVa enzyme (FIG. 1) and grown in the presence of hygromycin B. Forty colonies were selected and examined for the stable expression of PDE IVa enzyme. Two of the 40 clones selected displayed at least a 30-fold increase in cAMP hydrolytic activity compared to those cells which were transfected with a vector not containing the PDE IVa cDNA insert. As shown in FIG. 2a, the Km of the enzyme for cAMP as a substrate was determined to be 3.5 μM. The double-reciprocal plot (inset) of the enzyme activity versus substrate concentration revealed a single enzyme activity with a Vmax=19.5 nM cAMP hydrolyzed/mg. protein per min. Additionally, cAMP hydrolytic activity in the stable clones was completely inhibitable by 1 $\mu$M R-rolipram indicating the presence of a high affinity type IV cAMP dependent phosphodiesterase. The constitutive phosphodiesterase activity measured in control cells (VH2) grown in selection media did not exhibit any rolipram-sensitivity (data not shown). Eighty percent of the total PDE IVa enzyme activity was found to be in the soluble fraction of the cell sonicate. Western blot analysis of the soluble fraction using an anti PDE IVa antibody demonstrates the full-length expression of the PDE IVa enzyme with an apparent molecular mass of 125 KDa (FIG. 3a). Northern blot analysis of poly A RNA prepared from the stable transfectant revealed the presence of a 2700 bp transcript. No immunoreactive protein or mRNA transcripts encoding for the PDE IVa enzyme was detected in the VH2 control CHO-K1 cells by Western or Northern blot analysis, respectively.

Determination of Whole-Cell cAMP Content

Elevations in the cellular contents of cAMP in response to the PDE IV enzyme inhibitors were examined. Incubating the CHO-K1 PDE IVa stable clone with inhibitor alone had no measurable effect on the cellular levels of cAMP (not shown). In order to observe any appreciable increase in cAMP content, $PGI_2$ (10 FM) was included along with the PDE IV inhibitors in the incubation solution. $PGI_2$ alone caused a nominal 50% increase in basal cAMP levels in the cells. As shown in FIG. 4, RS 14203 was the most potent agent in elevating cellular cAMP from 0.2 pmol cAMP/$10^4$ cells to 3.6 pmols cAMP/$10^4$ cells (EC50=27 nM) followed by (R)-rolipram (EC50=486 nM). CDP 840 and (S)-rolipram were the least potent of the compounds tested, and a maximal "plateau" response was not obtained. An estimated 30-fold stereoselectivity between the (R) and (S) isomers of rolipram was noted. No significant changes in the VH2 CHO control cellular content of cAMP was observed with the inhibitors in either the presence or the absence of 10 $\mu$M $PGI_2$.

Effect of Selective PDE IV Inhibitors on cAMP Hydrolysis

Cells stably expressing PDE IVa enzyme activity were sonicated and the soluble and particulate fractions obtained through high-speed centrifugation. Inhibition of PDE IVa activity by the compounds was examined using the soluble fraction of the cells, since at least 80% of the total PDE IVa activity was localized to the cytosolic fraction. As shown in FIG. 5, RS 14203 and CDP 840 were equipotent at inhibiting the soluble PDE IVa activity both with $IC_{50}s$=9 nM. The (R) and (S) stereoisomers of rolipram were comparatively less potent with apparent IC50S of 110 nM and 420 nM, respectively. Compared to the whole-cell cAMP measurements where at least a 30-fold selectivity was observed between the two stereoisomers, only a 3- to 4-fold stereoselectivity was noted for the inhibition of PDE IVa enzyme. Additionally, the rank potencies of the compounds did not translate from the whole-cell cAMP measurements to the inhibition of enzyme activity as measured in the soluble fraction obtained from the cells.

Whole-Cell PKA Activation Ratios

The measured accumulation of cAMP in tissues has not always been a true reflection of the cellular changes which are brought about by hormones and neurotransmitters. Past reports have suggested that the lack of correlation between measured cellular changes and cAMP levels may result from compartmentalization of the second messenger. It has been suggested that by examining the cAMP dependent protein kinase activation ratio in the cell (21), changes in cellular cAMP in the relevant cellular compartments may be obtained. PKA activation ratios were examined in order to determine whether the ability of the compounds to inhibit the PDE IVa enzyme is better correlated with endpoint cellular changes. As shown in FIG. 6, the rank order potencies of the compounds to activate PKA in the cell was very similar to the rank order for their ability to elevate cAMP in the cells. It was determined that RS 14203 was more potent than (R)-rolipram>CDP 840>(S)-rolipram in mediating an activation of PKA phosphotransferase activity. The apparent EC50s of the four compounds to activate PKA were calculated to be 10 nM, 168 nM, 319 nM, and 1 $\mu$M, respectively. From these data, the lack of correlation between the rank potencies of the compounds when comparing the whole-cell data with the measured enzyme activity cannot be accounted for by cAMP compartmentalization.

Effect of Ionic Strength on PDE IV Inhibitor Potency

The effect of assay buffer ionic strength on the PDE IV inhibitor potencies was examined. As shown in FIG. 7, increasing the $MgCl_2$ in the assay buffer from 5 mM up to 100 mM results in an apparent increase in the potencies (reflected by the IC50 values) of (R)- and (S)-rolipram and RS14203 from 431 nM, >1000 nM and 140 nM, to 4 nM, 60 nM and 0.5 nM, respectively. The apparent $IC_{50}$ for CDP 840 was not substantially affected by the increase in $MgCl_2$ assay buffer. The increase in rolipram sensitivity exhibited by the PDE Iva enzyme at 100 mM $MgCl_2$ is not due to a specific divalent cation or anion requirement. As shown in FIG. 8, increasing the ionic strength of the assay buffer with either KCl, choline chloride or NaBr increases the PDE IVa enzyme sensitivity to (R)-rolipram in much the same manner that was seen with $MgCl_2$. The shift of the enzyme into a "high-affinity" state for (R)-rolipram is not dependent upon the assay solution osmolality, since concentrations of polyethylene glycol 200, mannitol or of sucrose up to 300 mOsm have no effect upon the rolipram sensitivity of the enzyme. The relationship between the ability of a group of PDE IV inhibitors to elevate cAMP in the CHO-K1 cells stably expressing the PDE IVa enzyme, versus the ability of this same group of compounds to inhibit the recombinant enzyme in a broken-cell preparation is shown in FIGS. 10a and b. There is a lack of concordance (FIG. 9) between the ability of a compound to elevate cAMP in the CHO-K1 cells and its biochemical potency as determined at a $MgCl_2$ concentration of 10 mM (r=0.46, p>0.05). However, as shown in FIG. 9, when the rank order of potencies for elevations of cAMP in the whole-cell assay and the inhibitory potencies for the same group of compounds obtained at 100 mM $MgCl_2$ are compared, a highly significant coefficient of correlation (r=0.70) is obtained (p<0.0001).

Characterization of Epitope FLAG PDE IVA and FLAG PDE $IV_{met330}$ Enzymes

Both the full-length PDE IVA and truncated PDE $IVA_{met330}$ FLAG-enzymes were eluted from the M2 affinity gel in the presence of 0.5 mg/ml FLAG peptide. Following a 4-fold concentration of the pooled column fractions exhibiting phosphodiesterase activity, the enzymes were subjected to SDS-PAGE and Coomassie blue staining. As shown in FIG. 11a, the full-length and truncated enzymes have been purified to apparent homogeneity using the FLAG expression system. The FLAG PDE IVA enzyme appears as a single band with a molecular mass of 125 KDa. The FLAG PDE $IVA_{met330}$ enzyme also appears as a single band but with a molecular mass of 85 KDa. These same protein bands are recognized by both antibodies directed against the catalytic domain of the PDE IVA enzyme and antibodies directed against the FLAG peptide as shown in FIGS. 11b and 11c, respectively.

The FLAG PDE IVA enzyme exhibits first-order kinetics with respect to substrate (FIG. 12a) with a $K_m$ of 2.9±0.4 mM cAMP and a Vm. of 9.7±0.2 mMol cAMP hydrolyzed/mg prot/min when assayed in the presence of 150 mM KCl. The truncated FLAG PDE IVA$_{met330}$ enzyme exhibits the same first-order kinetics (FIG. 12b) with a $K_m$ of 2.6±0.2 mM cAMP and a $V_{max}$ of 6.7+0.8 mMols cAMP hydrolyzed/mg prot/min in the presence of 150 mM KCl. Although the kinetics of the two enzymes are similar, their sensitivity to inhibition by (R)-rolipram differ significantly as outlined in Table II. (R)-Rolipram inhibits the full-length FLAG PDE IVA enzyme with an IC$_{50}$ of 111±43 nM (n=3±SEM). Approximately 10-times more (R)-rolipram is required to inhibit 50% of the FLAG PDEIVA$_{met330}$ catalytic activity (IC$_{50}$ =880 nM). The presence of 150 mM KCl in the assay buffer had no effect upon the measured $V_{max}$=for either FLAG enzyme tested.

Figure 13A:
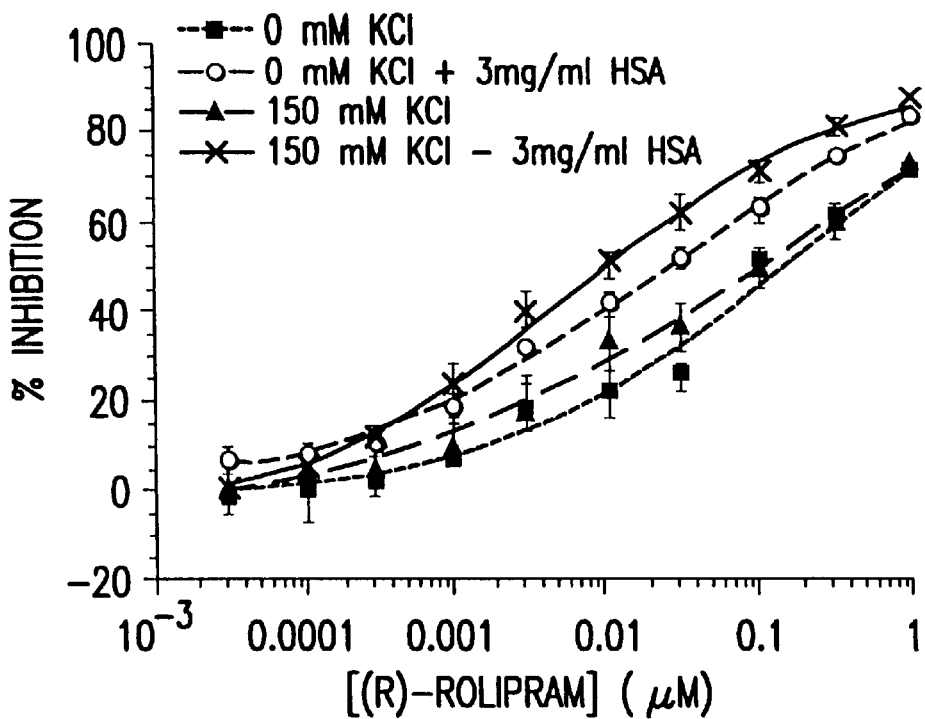
FIG. 13. Effect of KCl and HSA on FLAG PDE IVA and FLAG PDE IVA$_{met330}$ sensitivity to (R)-rolipram inhibition.

Effect of Ionic Strength and HSA on Sensitivity of Purified FLAG Enzymes to (R)-Rolipram Inhibition Unlike the wild-type PDE IVA enzyme obtained by stable expression in the CHO-K1 cells, the sensitivity of the FLAG PDE IVA enzyme to inhibition by (R)-rolipram is not dramatically shifted by the presence of 150 mM KCl in the assay buffer as shown in FIG. 13a (135 nM and 90 nM in the absence and presence of KCl, respectively). Interestingly, (R)-rolipram was much more potent (IC$_{50}$ =25 nM) against the enzyme activity when assayed in the presence of 3 mg/ml purified HSA. The shift in sensitivity of the enzyme to (R)-rolipram occured in concentrations of HSA as low as 0.1 mg/ml and was essentially maximal when the concentration of HSA in the enzyme assay buffer was increased to 1 mg/ml (not shown). The presence of 150 mM KCl in combination with 3 mg/ml HSA provided an additional 3-fold increase in enzyme sensitivity to (R)-rolipram (25 nM to 9 nM). The shift in the sensitivity of the FLAG PDE IVA enzyme to (R)-rolipram was accompanied by a modest but statistically significant (p<0.05) shift in the $K_m$ of the enzyme for cAMP and a 50% reduction in the $V_{max}$ (Table II). Neither HSA by itself nor in combination with 150 mM KCl had any effect on the binding of cAMP or 5'AMP to the SPA beads.

Figure 13B:
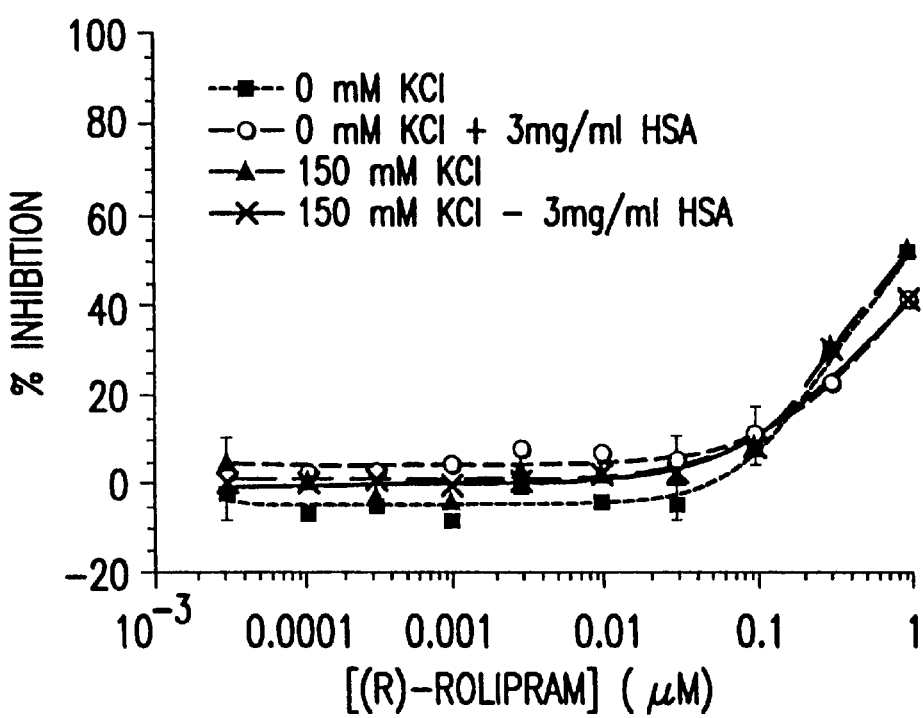

In contrast to the full-length FLAG PDE IVA enzyme, neither 150 mM KCl nor 3 mg/ml HSA alone or in combination was able to shift the sensitivity of the truncated FLAG PDE IVA$_{met330}$ enzyme for (R)-rolipram (FIG. 13b). The effects of the modifications to the assay buffer if any, tended to lower the affinity of the enzyme for (R)-rolipram since the extrapolated IC$_{50}$ shifted from 880 nM to 2633±738 nM (Table II). The $V_{max}$'s of the two enzymes were reduced by approximately 40% to 50% compared to control by the presence of 3 mg/ml HSA in the assay buffer. The catalytic activities for both enzymes remained first-order with respect to substrate in the presence of HSA (FIGS. 12a and 12b) and 150 mM KCl.

Effect of Ionic Strength and HSA on High-Affinity [$^3$H](R)-Rolipram Binding (S$_r$)

Figure 10D:
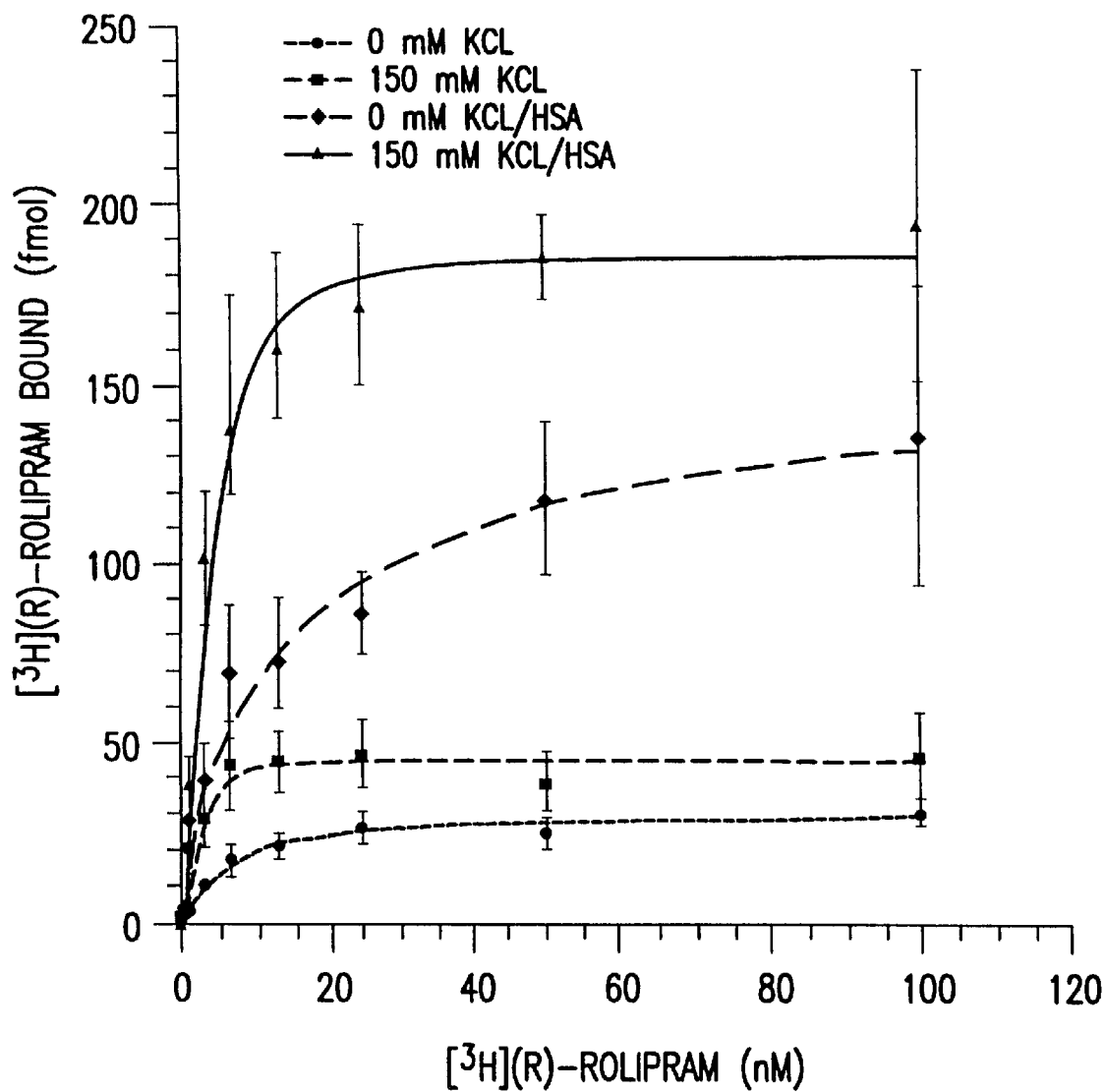
FIG. 10d–f. Effect of KCl and HSA on [$^3$H](R)-rolipram binding to FLAG PDE IVA enzyme.
Figure 10E:
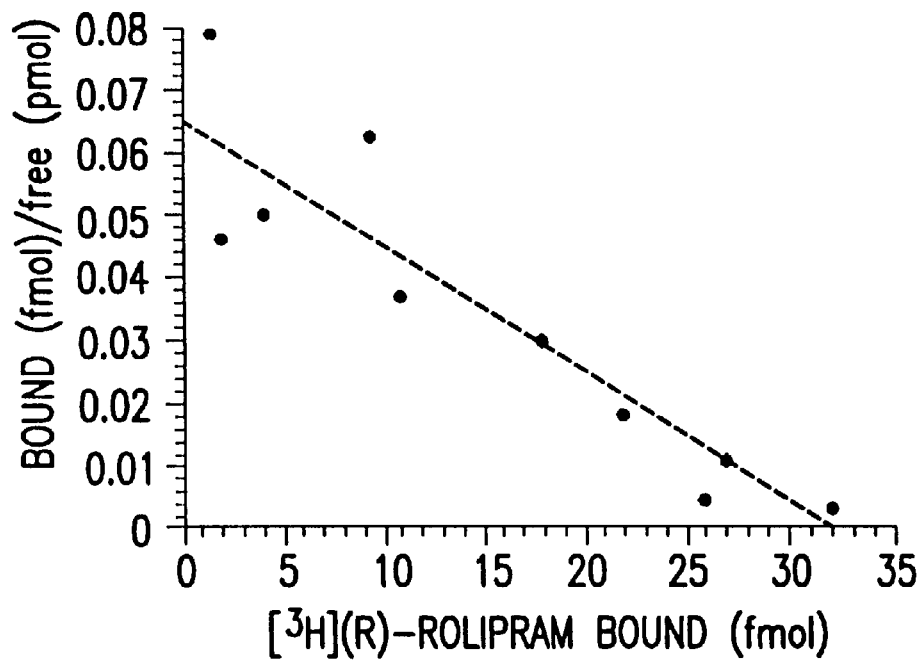

High-affinity [$^3$H](R)-rolipram binding was performed on both the purified FLAG PDE IVA$_{met330}$ and FLAG PDE IVA. The FLAG PDE IVA$_{met330}$ enzyme did not exhibit any saturable binding of [$^3$H](R)-rolipram over a concentration range of 0.2 to 100 nM (not shown). As shown in FIG. 10d, saturable binding was observed with the FLAG PDE IVA enzyme over the same range of concentrations of [$^3$H](R)-rolipram. The full-length enzyme bound ligand with a Kd of 0.4±0.1 nM (Table III), and a B$_{max}$ of 30 fmol resulting in a 0.02:1 stoichiometry. Scatchard analysis of the data (FIG. 10e) revealed the presence of a single class of high-affinity sites. Increasing the ionic strength of the binding buffer with 150 mM KCl doubled the B$_{max}$ to 63±16 fmol/1.6 pmol enzyme with an apparent Kd of 0.4±0.1 nM. In the presence of 3 mg/ml HSA the B$_{max}$ increased by 5-fold to 150±47 fmol/1.6 pmol enzyme, with a non-significant change in the Kd (Table III).

Figure 10F:
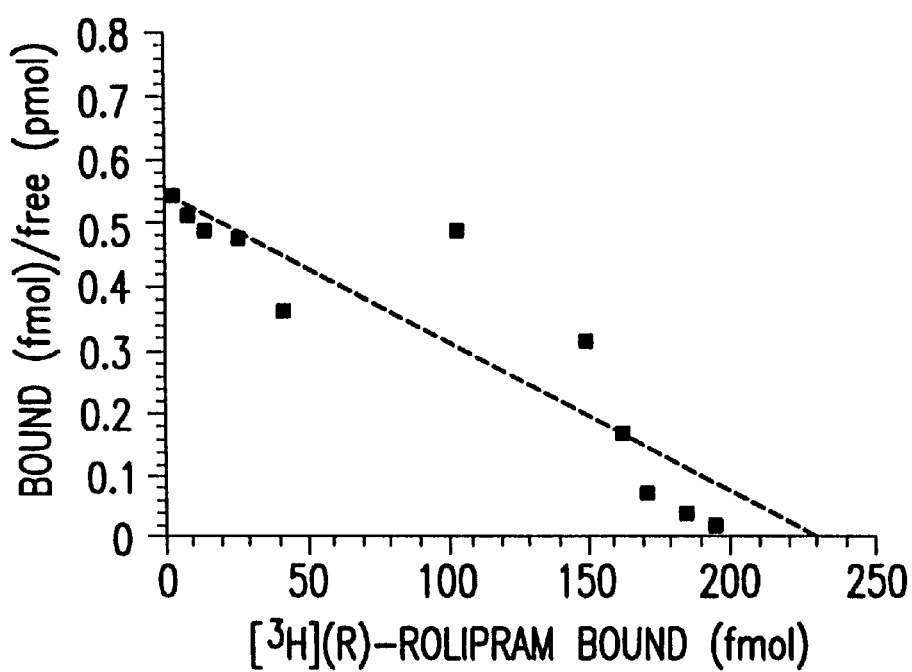

As shown in FIG. 10d, the purified FLAG PDE IVA enzyme exhibited an 8-fold increase in the saturable binding of [$^3$H](R)-rolipram in the combined presence of 3 mg/ml HSA and 150 mM KCl. Scatchard analysis of the data again reveals the binding of ligand to a single class of high- affinity sites (FIG. 10f) with a Kd of 0.4±0.1 nM and B$_{max}$ of 240 fmol/1.6 pmol purified enzyme. No specific binding of [$^3$H](R)-rolipram to the HSA was noted either in the presence or absence of 150 mM KCl. Additionally, presoaking the filtermats for 15 minutes in a solution containing 1 % PEI, 150 mM KCl and 3 mg/ml HSA had no effect upon the B$_{max}$ of the enzyme preparation.

Effect of Ionic Strength on [$^3$H](R)-Rolipram Binding (Sr)

High-affinity [$^3$H](R)-rolipram binding was performed on the soluble CHO-K1 PDE IVa enzyme in the presence of increasing ionic strength (FIG. 10a). Binding was saturable over a ligand concentration range of 0.2–100 nM. Nonspecific binding was insignificant, accounting for less than 5% of total binding. The amount of specific [$^3$H](R)-rolipram binding increased as the concentration of KCl in the assay buffer was varied from 0 mM to 300 mM. A Scatchard analysis of the data revealed that the soluble fraction bound [$^3$H](R)-rolipram with a total specific binding capacity (B$_{max}$) of 0.16 pmol/20 μg prot. and Kd=25 nM in the absence of added KCl in the assay (FIG. 10b). Increasing the ionic strength of the assay buffer with 150 mM KCl more than tripled the Bmax to 0.47 pmol/20 μg prot. with an apparent Kd of 17 nM (FIG. 10c). Based on reported catalytic activities for the purified PDE IVa enzyme, which range from 1 to 10 μM cAMP hydrolyzed/min/mg protein, the apparent stoichiometry of high-affinity [$^3$H](R)-rolipram binding was 0.2 to 2. The calculated stoichiometry of binding suggests a high efficiency of ligand-enzyme trapping by the polyethyleneimine treated filtermat. Interestingly, although the specific binding of [$^3$H](R)-rolipram to the enzyme extract at the lower KCl concentrations was best fitted to a single-site ligand-receptor interaction, the binding of [$^3$H](R)-rolipram to the enzyme at 300 mM KCl appeared to be co-operative with a Hill coefficient of 2.

Discussion

The potential utility of selective inhibitors of the PDE IV enzyme for the treatment of inflammatory airway diseases is an extremely attractive concept based on their biological profile in various in vitro and in vivo models of inflammation (22). The clinical development of potent and selective PDE IV inhibitors has in the past been hampered by the dose limiting side effects exhibited by these compounds in clinic. Compounds such as rolipram were found to have an extremely narrow therapeutic window as a result of profound episodes of nausea in patients. In order to examine and test for the clinical efficacy of PDE IV inhibitors, one must gain an understanding of how the biochemical potency of this class of compounds translates at the cellular and organ specific levels and, as well, the mechanistic basis for emesis.

Cellular changes are known to be mediated by alterations in the levels of second messengers such as cAMP. Agents are able to modulate cAMP levels in target tissues by either altering the rate of its synthesis through an activation of adenylyl cyclase or by affecting the rate of its metabolism via phosphodiesterase enzymes (23). Since cAMP is ubiquitously distributed throughout all mammalian tissues, indiscriminate pharmacological manipulation in the cellular content of this molecule would clearly lead to undesirable effects in a patient. A rekindling of interest has arisen in this field with the identification of a family of phosphodiesterase enzymes which are selective for cAMP and which are primarily expressed in cells thought to play a role in the inflammatory process(es). The PDE IV enzyme family is considered to be the biochemical target for a class of compounds typified by rolipram, and therefore, a clear biochemical and pharmacological understanding of how these agents act in vitro and in vivo would lead potentially to the development of the next generation of antiasthmatic and antiinflammatory drugs (2).

In comparison to other known PDE IV enzyme inhibitors, CDP 840 is as potent as RS 14203 and more potent than (R)-rolipram when assayed against the recombinant full-length PDE IVa enzyme. However, CDP 840 is consistently less potent than RS 14203 and (R)-rolipram at elevating whole-cell cAMP levels in eosinophils from guinea pigs, human neutrophils, and in HL-60 and U937 cells (data not presented). In order to better understand how the biochemical potencies of these compounds translate to changes in whole-cell cAMP levels, a CHO-K1 cell line stably expressing high levels of the PDE IVa enzyme was established. Since eosinophils and neutrophils contain more than one isoform of the PDE IV enzyme (6), it was thought that a better comparison could be made between the biochemical and whole-cell potencies using the stable CHO-K1 cell line. It was apparent that the sensitivity of the PDE IVa enzyme to inhibitors was quite different when comparing cAMP accumulation in the intact cell to inhibition of cAMP hydrolysis in a soluble preparation obtained from that same cell line. There are two plausible explanations which might account for these differences. Post-translational modification of PDE IV enzymes has been suggested by Conti and coworkers (24). However, in our study, preincubating CHO-K1 cells stably expressing the PDE Iva enzyme with phorbol esters, and/or phosphatase inhibitors (okadaic acid, tautomycin) had no effect on the sensitivity of the enzyme to inhibitors either in whole-cell or broken-cell preparations (data not shown). Souness et al. (25) have shown that either detergent solubilization or glutathione/vanadate treatment of guinea pig eosinophil membranes alters both the kinetics of the membrane bound PDE IV enzyme and the sensitivity of the catalytic activity to various known inhibitors. In their study, exposing the soluble enzyme to vanadate/glutathione had no further effects than solubilization itself. Since greater than 80% of the PDE IVa enzyme activity expressed in the CHO-K1 cells is soluble, any membrane effects on our enzyme would be insignificant.

In many instances, investigators have suggested that measurements of intracellular cAMP may be an insensitive index of altered cellular function brought about via the cAMP kinase cascade. This lack of sensitivity may, at least in part, result from compartmentalization of the cyclic nucleotide (23). Determinations of PKA activation ratios and/or protein phosphorylation as monitored by incorporation of 32P into an endogenous cellular protein are thought to be more sensitive and relevant to the in vivo hormonal modulation of intracellular cAMP. To determine whether the lack of correlation between the ability of an inhibitor to elevate cAMP in the whole cells versus its biochemical potency on the enzyme might be due to cAMP compartmentalization, PKA activation ratios were measured. It was observed that the ability of the compounds to activate PKA in the cells mirrored their ability to cause an accumulation of cAMP in the cells. The PKA activation assay, however, was found to be more sensitive than assaying changes in whole-cell cAMP levels. The inhibitors were able to mediate an activation of the kinase in the presence of 1 $\mu$M PGI$_2$, whereas at least 10 $\mu$M PGI$_2$ was required to observe any increase in whole-cell cAMP with the inhibitors. The EC$_{50}$s obtained for the compounds from the two assays, however, were closely similar.

Since the measurements of PDE IVa catalytic activity are performed by first lysing the cells and diluting out the intracellular constituents, we examined the effects of approximating the intracellular milieu by increasing the concentration of salt in the PDE IV assay buffer. Under these conditions, it was observed that RS 14203, (R)-rolipram and (S)-rolipram became more potent at inhibiting the recombinant enzyme when compared to their potencies obtained in the presence of little or no salt in the assay. In comparison, the IC50 for CDP 840 was not appreciably affected with increasing amounts of salt in the assay. Thus, the rank order of potencies of the inhibitors to inhibit the phosphodiesterase enzyme under assay conditions resembling the ionic strength found in the intact cell closely reflects their ability to elevate cAMP in the whole-cell assay. Additionally, the apparent stereoselectivity of (R) and (S)-rolipram observed in the whole-cell is recovered with the soluble enzyme under high salt conditions. It would appear, therefore, that the lack of correlation between the biochemical potencies of the inhibitors on the enzyme and their ability to elevate cAMP in the whole-cell results from the inability the recreate the intracellular environment in which the PDE IVa enzyme exists normally.

Mixed inhibitory kinetics have been observed by Livi et al. (26,27) for rolipram (racemic) with respect to a full-length PDE Iva enzyme. Additionally, it was reported that the Hill co-effecient for (R)-rolipram inhibition of the HPDE IV catalytic activity was equal to 0.43. Together, these data suggest that (R)-rolipram might be inhibiting a mixture of both "high" and "low" affinity conformations of the enzyme. Since the amino acid sequence of our PDE IVa enzyme shares 99.7% identity with the sequence reported by Livi et al., (26) it is not surprising that our observations are consistent with their data. In our study, the sensitivity of the PDE IVa enzyme to inhibition by certain compounds was enhanced as the ionic strength of the assay buffer was increased. Co-incidentally, an increase in the capacity for high-affinity [$^3$H](R)-rolipram binding by the enzyme was observed along with the shift in rrolipram sensitivity. These data support the notion that the Sr and Sc sites are not two distinct domains on the enzyme. Additionally, the capacity of [$^3$H](R)-rolipram binding displayed by an enzyme preparation is an index of the proportion of that enzyme in either a high-affinity or low-affinity conformational states for rolipram.

Contrary to our findings and to those reported by Livi et al., Sullivan and colleagues (28) have shown that rolipram behaves as a simple competitive inhibitor with respect to substrate on a PDE Iva enzyme (PDE IVh6.1) expressed in either *S. cerevisiae* or COS-1 cells. The authors attribute the observed differences in inhibitory kinetics for rolipram to the substitution of 5 amino acids contained close to the catalytic domain within the Livi sequence. The substitutions which Sullivan et al. refer to were, however, a consequence of sequencing errors which have now been corrected and entered into the Genebank database (personal communication, T. Torphy). To this effect, the Livi sequence now shares 98.7% identity with that of PDE IVh6.1. The remaining amino acids which do not show identity are found well outside of the conserved PDE IVa catalytic domain. The differences observed by Sullivan et al., for rolipram might well be due to the additional 150 N-terminal amino acids contained on the full-length Livi enzyme. Since the N-terminal is proposed to confer high affinity rolipram (Sr) binding upon the PDE IVa enzyme, a truncation of the N-terminus may modify an interaction of the enzyme with respect to selective inhibitors (29).

Data from our laboratory show that truncation of the PDE IVa enzyme to a form which is still catalytically active but fails to bind rolipram with high-affinity, and as well, exhibits low sensitivity to inhibition by rolipram, is not affected by ionic strength in the same manner as the full-length version. These data suggest that the N-terminus of the enzyme, although not containing a distinct high-affinity rolipram binding site, does confer a high-affinity state upon the enzyme via ionic interactions. It remains unclear as to why the inhibitory potencies of some compounds, such as CDP 840, are not affected by an increase of ionic strength in the assay buffer.

It has been suggested that inhibition of a "high-affinity" form of the PDE IV enzyme is related to dose-limiting side effects observed in vivo for these compounds. These dose-limiting side-effects include potentiation of gastric acid secretion, nausea and vomiting. In addition, inhibition of a "low-affinity" form of the enzyme is thought to be correlated with the potentially therapeutic aspects for this class of compound (31,32). Surprisingly, we have found that the "high-affinity" and "low-affinity" forms of the enzyme are simply artifacts which result from the conditions in which these two conformations of the enzyme are assayed.

The ability of an inhibitor to elevate whole-cell cAMP is not only dictated by its biochemical potency, but also its membrane permeability. Thus, it would appear that the whole-cell assay described here bridges the gap between the measured biochemical potency of an inhibitor and its ability to increase cAMP levels in a relevant target tissue. We believe that one key element for the development of PDE IV enzymes inhibitors is to determine whether the measured in vitro potency tracks with the in vivo potency for a compound.

In summary, we have determined that the lack of agreement between whole-cell potencies and biochemical potencies for a given set of compounds as it relates to PDE IVa inhibition is attributed to the assay conditions under which these compounds are studied. We have also shown that the notion of the existence of distinct Sr and Sc domains on the enzyme is incorrect. In addition, this transfected cell line stably expressing PDE IVa will prove to be an extremely useful tool which will allow us to predict in vivo efficacy (anti-asthmatic, anti-inflammatory) for a compound in man when administered via the oral route.

Cellular changes are mediated by alterations in the levels of second messengers such as cAMP. Agents can modulate cAMP levels in target tissues either by altering the rate of cAMP synthesis through an activation of adenylyl cyclase or by affecting the rate of cAMP metabolism via phosphodiesterase enzymes (47). Since cAMP is ubiquitous to all mammalian tissues, indiscriminate pharmacological manipulation in the cellular content of this second messenger would clearly lead to undesirable effects in a patient. A rekindling of interest in the cAMP field has arisen with the identification of a family of phosphodiesterase enzymes which are predominately expressed in cells thought to play a role in asthma and inflammatory processes. The PDE IV enzyme family is considered to be the biochemical target for a class of compounds typified by rolipram. A clear biochemical and pharmacological understanding of how these agents act in vitro and in vivo might potentially lead to the development of a new generation of antiasthmatic and antiinflammatory drugs (2).

The biochemical mechanism by which rolipram is thought to act in the treatment of endogenous depression is via selective inhibition of cAMP dependent phosphodiesterase activity (49). It was shown that micromolar concentrations of rolipram inhibited the cAMP PDE activity found in membraneous and cytosolic fractions prepared from rat brain. Schneider et al (44), later reported that rat forebrain membranes contained a high density of saturable high-affinity ($\pm$)[3H] rolipram binding sites. These sites bound ($\pm$)[3H] rolipram with a Kd of 1.2 nM and $B_{max}$ of 19.3 pmol/g rat forebrain. It was thought that this binding site was related to PDE enzymes confined to the CNS, but the >1000-fold difference between the measured Kd and $IC_{50}$ for rolipram in the binding and enzymatic assays, respectively, raised doubt as to the involvement of a single common enzyme. Since the report of these data, a tremendous amount of time and effort has been invested to gain an understanding of the biochemical and pharmacological natures of the "high-affinity rolipram binding site" or Sr (35–39). The co-expression of high-affinity rolipram binding and Type IV PDE activity in yeast is indicative that the Sr and Sc are properties of the same enzyme (38). Additionally, the stoichiometry of [$^3$H](R)-rolipram binding to purified PDE IVA enzyme has indicated that only a small fraction of the total enzyme exhibits a high-affinity binding site (42). Together, the findings that the relative potencies for some compounds at displacing [$^3$H](R)-rolipram versus their ability to inhibit the catalytic activity differed, suggests that the two sites are functionally distinct (35, 37, 38). Functional mapping studies of the PDE IVA enzyme indicate that amino acids 265–332 may either form a high-affinity binding site that is outside of the catalytic domain or may be required for the recombinant enzyme to assume a conformation that binds rolipram at the catalytic domain with a high affinity (40). Our data would support the notion that the amino terminus of PDE IVA, which contains both UCR 1 and UCR 2 domains, allows the catalytic domain to assume a conformation which binds rolipram with high-affinity. By increasing the ionic strength in the enzymatic assay we determined that the soluble unpurified PDE IVA catalytic activity converted from a low- to a high-sensitivity to inhibition by (R)-rolipram. The salt dependent shift in $IC_{50}$ from low to high affinity was also measured for (S)-rolipram and RS 14203. Interestingly, the potency of CDP 840 was not affected by the increases in assay buffer ionic strength. The maximal potency of (R)-rolipram was observed at ionic strengths not dissimilar to that found in the cytosol of intact cells. Subjecting the unpurified cytosolic PDE IVA enzyme to size exclusion chromatography on a Superose 12 column resulted in the elution of a single peak of rolipram-sensitive activity with a molecular size corresponding to 115 KDa. Elution of the same material on the column following reequilibration with a buffer containing 300 mM KCl did not change the elution profile, suggesting that the salt effect confering the high- and low-sensitivity states of the PDE IVA enzyme to (R)-rolipram was not due to changing aggregation states of the protein (not shown). The 20-fold increase in high-affinity [3H]($\pm$)-rolipram binding to rat forebrain membranes observed in the presence of 100 mM NaCl and 1 mM $MgCl_2$ reported by Schneider et al (44), would support our findings that the catalytic state of the PDE WVA enzyme is capable of shifting from a low-affinity to a high-affinity conformer for rolipram.

To determine whether the low-afinity to high-affinity shifts in the catalytic state of the PDE IVA enzyme was due to direct interaction of salt with the enzyme or via alterations in kinase or phophatase activities (43), a FLAG expression construct was engineered which allowed us to characterize purified PDE IVA enzyme. It was observed that shifts in the (R)-rolipram sensitivity of the FLAG PDE IVA enzyme activity was dependent upon both assay buffer ionic strength and the presence of exogenous protein such as HSA or g-globulin (not shown). The nominal salt-induced shift in (R)-rolipram sensitivity observed with the FLAG PDE IVA enzyme compared to the complete high-affinity conversion of the crude cytosolic PDE IVA enzyme would suggest that the switching between low- and high-affinity conformers is dependent upon both ionic and protein-protein interactions which are unlikely to involve the activity of a phosphatase and/or kinase. Additionally, the increase in potency for (R)-rolipram against the FLAG PDE IVA catalytic activity is probably not due to alterations in the physical chemical properties of (R)-rolipram since the FLAG PDE $IV_{met330}$ was unaffected by these same changes in buffer composition. The buffer modifications used in the enzymatic assay also affected the behavior of the purified FLAG PDE IVA enzyme in the high-affinity [$^3$H](R)-rolipram binding assay. The enzyme exhibited an increased capacity to bind [$^3$H] (R)-rolipram with high-affinity when either the ionic strength or protein concentration was increased. The 8-fold increase in Box at 150 mM KCl and 3 mg/ml HSA would support the notion that the catalytic activity is capable of adopting a high affinity conformation with respect to inhibition by rolipram. If 100% of the enzyme however, were in a high-affinity conformation, we might have expected that the stoichiometry would be higher than the observed 0.15:1. The filter binding assay used in this study is not an equilibrium method for determining (R)-rolipram binding and therefore the stoichiometry may be affected. If (R)-rolipram has a fast off rate or freely dissociates during the filter wash steps this could result in the observed low stoichiometries. An increase in the $B_{max}$ of high-affinity (R)-rolipram binding might also arise through an activation of a high-affinity enzyme population as was shown by Sette et al.(43). This explanation would seem unlikely since the measured $V_{max}$ decreased by approximately 50%. To our knowledge, this is the first report showing that an elevation in PDE IVA high-affinity [$^3$H](R)-rolipram binding is accompanied by increased catalytic sensitivity to (R)-rolipram.

Deletion analysis of both the UCR1 and UCR2 domains results in a truncated PDE IV enzyme which retains rolipram-sensitive catalytic activity (40). The activity of the catalytic portion of the enzyme requires at least a micromolar concentration of (R)-rolipram for inhibition and exhibits no detectable saturable high-affinity rolipram binding. Since the sensitivity of the FLAG PDE $IVA_{met330}$ enzyme to (R)-rolipram was not modified by any of the different assay conditions tested, and that the enzyme does not display any saturable high-affinity [$^3$H](R)-rolipram binding, we must conclude that the upstream N-terminus regions of the PDE IVA enzyme are essential in allowing the catalytic domain of the enzyme to adopt either a low-affinity or a high-affinity conformation with respect to (R)-rolipram. It is unclear as to the mechanism by which ionic and protein interactions might facilitate the isotype switching of a low and high affinity conformer. The UCR1 region appears to harbor distinct hydrophillic and hydrophobic domains whereas UCR2 is predominately hydrophillic. By using yeast two hybrid systems, Houslay et al.(50) have reported that UCR1 and UCR2 are able to interact suggesting that the N-terminus may be involved in establishing distinct tertiary structures. These tertiary structures may then impact upon the catalytic conformation of the enzyme with respect to activity and inhibitor sensitivity. Switching of the PDE IV enzyme from low-affinity to high-affinity with respect to rolipram has also been shown by treating the enzyme with vanadate/glutathione (39). Together, all these data support the concept that the high-affinity rolipram binding site is a consequence of interconvertible catalytic states of the enzyme which can exhibit either high or low sensitivity to inhibition by rolipram.

It is of interest to note that even though the truncated PDE $IvA_{met330}$ enzyme is "locked" in a low-affinity conformation with respect to rolipram, some compounds such as CDP 840 do not discriminate between the two affinity states of the enzyme. Similar findings have been reported for RP 73401 (40) which exhibits a single class of high-affinity binding sites on the PDE IVA enzyme and various deletion mutants.

Since the PDE IVA enzyme is able to adopt either high or low affinity conformers, the question arises as to which state of the enzyme is relevant in a whole-cell setting. It would appear at least from our study that an inhibition of the high-affinity conformer is responsible for elevations of whole-cell cAMP in CHO-K1 cells. Given that the concentrations of KCl and protein required for the enzyme to adopt a high-affinity state are not excessively high compared to that which is normally found in an intact cell this conclusion is not too surprising for a simple expression system. Reports have, however, shown that in general, the compounds which are potent against the high-affinity binding site (Sr) have a greater potential for undesirable side-effects, whereas inhibition of a low affinity catalytic conformer relates to the therapeutic potential for Type IV PDE inhibitors (36, 37). A level of uncertainty is introduced when comparing differences between functional changes in tissues with either an inhibition of catalytic activity or the displacement of [3H]-rolipram by inhibitors. Since peripheral tissues and cells have been noted not to contain a high density of specific high-affinity rolipram binding sites, either mouse or rat brain membrane preparations have been used to asess a compound's affinity through the displacement of [$^3$H](R)-rolipram. Additionally, in order to assess the potency of a compound against the catalytic activity of the PDE IV enzyme, recombinant PDE IVA enzyme has been utilized in the assays. These comparisons between the inhibition of a known enzyme and binding of [$^3$H](R)-rolipram to a membrane preparation which has not been characterized with regards to the PDE IV isoform profile are further complicated when it is not known as to which of the 4 PDE IV isoforms actually modulates an end-point cellular or tissue functional readout. A more recent study by Kelly et al. (51), has shown that elevations in guinea pig macrophage cAMP can be correlated with either an inhibition of a high-affinity enzyme preparation obtained from the same cells when treated with Vo/2.GSH or with the displacement of high-affinity rolipram binding, again from the same source. These data support the view that an inhibition of a high-affinity enzyme is relevant to an accumulation of cAMP within these cells. If the activation state of these cells was intimately related to the cellular levels of cAMP then one might conclude that the compounds which are most potent against the high-affinity state are the most potent inhibitors of inflammation and as well, exhibit the highest potential for dose-limiting side-effects. It is unclear as to whether it will be possible to design inhibitors which posses antiasthmatic and antiinflammatory properties as well as a low emetogenic potential in man. Our data would suggest that compounds potent against the high-affinity conformation are more potent at inhibiting the activation of inflammatory cells if one accepts that elevations in whole-cell cAMP are a valid index. These compounds however, would also tend to exhibit the greatest potential for untoward CNS and gastrointestinal side effects. Given that there exist at least 4 distinct PDE IV isoforms and that each isoform has been shown to give rise to a number of splice variants, which in themselves can exhibit different cellular localization and affinities for inhibitors (47), this conclusion would be an oversimplification of the mechanism by which PDE IV inhibitors act.

In conclusion, this is the first report however, to demonstrate that interconversion of the PDE IVA enzyme activity from a low-affinity to a high-affinity conformer with respect to (R)-rolipram is associated with an increase in the high affinity binding capacity of the enzyme. Additionally, the interconversion of the enzyme induced by ionic and protein is dependent upon the two conserved upstream domains found on the HSPDE4A4B enzyme.

REFERENCES

1. Beavo, J. A.: Cyclic Nucleotide Phosphodiesterases: Functional Implications of Multiple Isoforms. Physiol. Rev.: 75, 725–748, 1995.
2. Barnes, P. J.: Cyclic nucleotides and phosphodiesterases and airway function. Eur. Respir. J.: 8, 457–462, 1995.
3. Beavo, J. A., Conti, M., and Heaslip, R. J.: Multiple Cyclic Nucleotide Phosphodiesterases. Mol. Pharmacol.: 46, 399–405, 1994.
4. Horton, Y. M., Sullivan, M., and Houslay, M. D.: Molecular cloning of a novel splice variant of human type IVA (PDE-IVA) cyclic AMP phosphodiesterase and localization of the gene to the p13.1-q12 region of human chromosome. Biochem. J.: 308, 683–691, 1995.
5. Manganiello, V. C., Murata, T., Taira, M., Belfrage, P., and Degerman, E.: Diversity in Cyclic Nucleotide Phosphodiesterase Isoenzyme Families. Arch. Biochem. Biophys.: 322, 1–13, 1995.
6. Engels, P., Fichtel, K., and Lubbert, H.: Expression and regulation of human and rat phosphodiesterase type IV isogenes. FEBS Letts.: 350, 291–295, 1994.
7. Schudt, C., Tenor, H., and Hatzelmann, A.: PDE isoenzymes as targets for anti-asthma drugs. Eur. Respir. J.: 8, 1179–1183, 1995.
8. Molnar-Kimber, K., Yonno, L., Heaslip, R., and Weichman, B.: Modulation of TNFa and IL-1 from endotoxin-stimulated monocytes by selective PDE isozyme inhibitors. Agents Actions: C77–C79, 1993.
9. Lagente, V., Moodley, I., Perrin, S., Mottin, G., and Junien, J. L.: Effects of isozyme-selective phosphodiesterase inhibitors on eosinophil infiltration in the guinea-pig lung. Eur. J. Pharmacol.: 255, 253–256, 1994.
10. Wright, C. D., Kuipers, P. J., Kobylarz-Singer, D., Devall, L. J., Klinkefus, B. A., and Weishaar, R. E.: Differential inhibition of human neutrophil functions; role of cyclic AMP-specific, cyclic GMP-insensitive phosphodiesterase. Biochem. Pharmacol.: 40, 699–707, 1990.
11. Fonteh, A. N., Winkler, J. D., Torphy, T. J., Heravi, J., Undem, B. J., and Chilton, F. H.: Influence of Isoproterenol and Phosphodiesterase Inhibitors on Platelet-Activating Factor Biosynthesis in the Human Neutrophil. J. Immunol.: 151, 339–350, 1993.
12. Holbrook, M., and Hughes, B.: The effect of rolipram and SK&F 94120 on ozone induced bronchial hyperreactivity to inhaled histamine in guinea pigs. Brit. J. Pharmacol.: 107, 245P, 1992.
13. Barnette, M. S., Grous, M., Cieslinski, L. B., Burman, M., Christensen, S. B., and Torphy, T. J.: Inhibitors of Phosphodiesterase IV (PDE IV) Increase Acid Secretion in Rabbit Isolated Gastric Glands: Correlation Between Function and Interaction with a High-Affinity Rolipram Binding Site. J. Pharmacol. Exper. Ther.: 273, 1396–1402, 1995.
14. Schneider, H. H., Yamaguchi, M., Andrews, J. S., and Stephens, D. N.: Discriminative Stimulus Properties of the Steroisomers of the Phosphdiesterase Inhibitor Rolipram. Pharmacol. Biochem. Behavior: 50, 211–217, 1995.
15. Watson, J. W., Gonsalves, S. F., Fossa, A. A., McLean, S., Seeger, T., Obach, S., and Andrews, P. L.: The antiemetic effects of CP-99,994 in the ferret and the dog: role of the NK1 receptor. Brit. J. Pharmacol.: 115, 84–94, 1995.
16. Houslay, M. D.: Compentalization of Cyclic AMP Phosphodiesterases, Signalling Crosstalk', Desensitization and the Phosphorylation of Gi-2 Add Cell Specific Personalization to the Control of the Levels of the Second Messenger Cyclic AMP. Advan. Enzyme Regul.: 35, 303–338, 1995.
17. Zhou, H. L., Newsholme, S. J., and Torphy, T. J.: Agonist-Related Differences in the Relationship Between cAMP Content and Protein Kinase Activity in Canine Trachealis. J. Pharmacol. Exp. Ther.: 261, 1260–1267, 1992.
18. Dent, G., Giembycz, M. A., Evans, P. M., Rabe, K. F., and Barnes, P. J.: Suppression of Human Eosinophil Respiratory Burst and Cyclic AMP Hydrolysis by Inhibitors of Type IV Phosphodiesterase: Interaction with the Beta Adrenoceptor Agonist Albuterol. J. Pharmacol. Exp. Ther.: 271, 1167–1174, 1994.
19. Cheng, H. C., Kemp, B. E., Pearson, R. B., Smith, A. J., Misconi, L., Van Patten, S. M., and Walsh, D. A. A potent synthetic peptide inhibitor of the cAMP-dependent protein kinase. J. Biol. Chem.: 261, 989–992, 1986.
20. Boie, Y., Rushmore, T. H., Darmongoodwin, A., Gregorczyk, R., Slipetz, D. M., Metters, K. M., and Abramovitz, M. Cloning and expression of a cDNA for the human prostanoid IP receptor. J. Biol. Chem.: 269, 12173–12178, 1994.
21. Corbin, J. D., Sugden, P. H., Lincoln, T. M., and Keely, S. L.: Compartmentalization of Adenosine 3':5'-Monophosphate and Adenosine 3':5'-Monophosphate-dependent Protein Kinase in Heart Tissue. J. Biol. Chem.: 11, 3854–3861, 1977.
22. Dent, G., and Giembycz, M. A. Selective Phosphodiesterase Inhibitors in the Therapy of Asthma. Clin. Immunother.: 3, 423–437, 1995.
23. Houslay, M. D., Scotland, G., Pooley, L., Spence, S., Wilkinson, I., McCallum, F., Julien, P., Rena, N. G., Michie, A. M., Erdogan, S., Zeng, L., O'Connel, J. C., Tobias, E. S., and MacPhee, I. Alternative splicing of the type-IVA cyclic AMP phosphodiesterase gene provides isoform variants with distinct N-terminal domains fused to a common, soluble catalytic unit: designer' changes in Vmax, stability and membrane association. Biochem. Soc. Trans.: 23, 393–398, 1995.
24. Sette, C., Vicini, E., and Conti, M. The ratPDE3/IVD phosphodiesterase gene codes for multiple proteins differentially activated by cAMP-dependent protein-kinase. J. Biol. Chem.: 269, 18271–18274, 1994.
25. Souness, J. E., Maslen, C., Webber, S., Foster, M., Raeburn, D., Palfreyman, M. N., Ashton, M. J., and Karlsson, J. A. Suppression of eosinophil function by RP 73401, a potent and selective inhibitor of cyclic AMP-specific phosphodiesterase: comparison with rolipram. Brit. J. Pharmacol.: 115, 39–46, 1995.

26. Livi, G. P., Kmetz, P., McHale, M. M., Cieslinski, L. B., Sathe, G. M., Taylor, D. P., Davis, R. L., Torphy, T. J., and Balcarek, J. M. Cloning and Expression of cDNA for a Human Low-Km, Rolipram-Sensitive Cyclic AMP Phosphodiesterase. Mol. Cell. Biol.: 10, 2678–2686, 1990.
27. Torphy, T. J., Stadel, J. M., Burman, M., Cieslinski, L. B., McLaughlin, M. M., White, J. R., and Livi, G. P. Coexpression of Human cAMP-specific Phosphodiesterase Activity and High Affinity Rolipram Binding in Yeast. J. Biol. Chem.: 267, 1798–1804, 1992.
28. Sullivan, M., Egerton, M., Shakur, Y., Marquardsen, A., and Houslay, M. D. Molecular cloning and expression, in both COS-1 cells and S. Cerevisiae, of a human cytosolic type-IVA, cyclic AMP specific phosphodiesterase (hPDE-IVA-h6.1). Cell. Signalling: 6, 793–812, 1994.
29. Torphy, T. J., DeWolf, W. E., Green, D. W., and Livi, G. P. Biochemical characteristics and cellular regulation of phosphodiesterase IV. Agents and Actions: supp43, 51–71, 1993.
30. Bolger, G., Michaeli, T., Martins, T., St. John, T., Steiner, B., Rodgers, L., Riggs, M., Wigler, M., and Ferguson, K. A family of human phosphodiesterases homologous to the Dunce learning and memory gene product of Drosophila melanogaster are potential targets for antidepressant drugs. Mol. Cell. Biol. 13, 6556–6571, 1993.
31. Barnette, M. S., Manning, C. D., Cieslinski, L. B., Burman, M., Christensen, S. B., and Torphy, T. J. The ability of phosphodiesterase IV inhibitors to suppress superoxide production in guinea pig eosinophils is correlated with inhibition of phosphodiesterase IV catalytic activity. J. Pharmacol. Exp. Ther. 273, 674–679, 1995.
32. Barnette, M. S., O'Leary Bartus, J., Burman, M., Christensen, S. B., Cieslinski, L. B., Esser, K. M., Prabhaker, U. M., Rush, J. A., and Torphy, T. J. Association of the anti-inflammatory activity of phosphodiesterase 4 (PDE4) inhibitors with either inhibition of PDE4 catalytic activity or competition for [3H]rolipram binding. Biochem. Pharmacol. 51, 949–956, 1996.
33. Beavo, J. A.: Cyclic Nucleotide Phosphodiesterases: Functional Implications of Multiple Isoforms. Physiol. Rev.: 75, 725–748, 1995.
34. Livi, G. P., Kmetz, P., McHale, M. M., Cieslinski, L. B., Sathe, G. M., Taylor, D. P., Davis, R. L., Torphy, T. J., and Balcarek, J. M. Cloning and Expression of cDNA for a Human Low-$K_m$, Rolipram-Sensitive Cyclic AMP Phosphodiesterase. Mol. Cell. Biol.: 10, 2678–2686, 1990.
35. Barnette, M. S., Grous, M., Cieslinski, L. B., Burman, M., Christensen, S. B., and Torphy, T. J.: Inhibitors of Phosphodiesterase IV (PDE IV) Increase Acid Secretion in Rabbit Isolated Gastric Glands: Correlation Between Function and Interaction with a High-Affinity Rolipram Binding Site. J. Pharmacol. Exper. Ther.: 273, 1396–1402, 1995.
36. Barnette, M. S., O'Leary Bartus, J., Burman, M., Christensen, S. B., Cieslinski, L. B., Esser, K. M., Prabhaker, U. M., Rush, J. A., and Torphy, T. J. Association of the anti-inflammatory activity of phosphodiesterase 4 (PDE4) inhibitors with either inhibition of PDE4 catalytic activity or competition for [$^3$H]rolipram binding. Biochem. Pharmacol. 51, 949–956, 1996.
37. Barnette, M. S., Manning, C. D., Cieslinski, L. B., Burman, M., Christensen, S. B., and Torphy, T. J. The ability of phosphodiesterase IV inhibitors to suppress superoxide production in guinea pig eosinophils is correlated with inhibition of phosphodiesterase IV catalytic activity. J. Pharmacol. Exp. Ther. 273, 674–679, 1995.
38. Torphy, T. J., Stadel, J. M., Burman, M., Cieslinski, L. B., McLaughlin, M. M., White, J. R., and Livi, G. P. Coexpression of Human cAMP-specific Phosphodiesterase Activity and High Affinity Rolipram Binding in Yeast. J. Biol. Chem.: 267, 1798–1804, 1992.
39. Souness, J. E., Maslen, C., Webber, S., Foster, M., Raeburn, D., Palfreyman, M. N., Ashton, M. J., and Karlsson, J. A. Suppression of eosinophil function by RP 73401, a potent and selective inhibitor of cyclic AMP-specific phosphodiesterase: comparison with rolipram. Brit. J. Pharmacol.: 115, 39–46, 1995.
40. Jacobitz, S., McLaughlin, M. M., Livi, G. P., Burman, M., and Torphy, T. J. Mapping the functional domains of human recombinant phosphodiesterase 4A: Structural requirements for catalytic activity and rolipram binding. Mol. Pharmacol. 50, 891–899, 1996.
41. Rocque, W. J., Holmes, W. D., Patel, I. R., Dougherty, R. W., Ittoop, O., Overton, L., Hoffman, C. R., Wisely, G. B., Willard, D. H., and Luther, M. A. Detailed characterization of a purified type 4 phosphodiesterase, HSPDE4B2B: Differentiation of high- and low-affinity (R)-rolipram binding. Prot. Expres. Purif. 9, 191–202, 1997.
42. Hughes, B., Owens, R., Perry, M., Warrellow, G., Allen, R. PDE 4 inhibitors: the use of molecular cloning in the design and development of novel drugs. Drug Discov. Today, 2, 89–101, 1997.
43. Sette, C., Vicini, E., and Conti, M. The rat PDE3/WD phosphodiesterase gene codes for multiple proteins differentially activated by cAMP-dependent protein-kinase. J. Biol. Chem.: 269, 18271–18274,1994.
44. Schneider, H. H., Yamaguchi, M., Andrews, J. S., and Stephens, D. N.: Discriminative Stimulus Properties of the Steroisomers of the Phosphodiesterase Inhibitor Rolipram. Pharmacol. Biochem. Behavior: 50, 211–217, 1995.
45. Pon, D. J., Boulet, L., Cirino, M., Muise, E. S., and Rodger, I. W. Characterization of rabbit polyclonal anti-peptide antibodies directed against Type IV phosphodiesterase isoenzymes. Amer. J. Resp. Crit. Care Med. 155, A612, 1997.
46. Boie, Y., Rushmore, T. H., Darmongoodwin, A., Gregorczyk, R., Slipetz, D. M., Metters, K. M., and Abramovitz, M. Cloning and expression of a cDNA for the human prostanoid IP receptor. J. Biol. Chem.: 269, 12173–12178, 1994.
47. Houslay, M. D., Scotland, G., Pooley, L., Spence, S., Wilkinson, I., McCallum, F., Julien, P., Rena, N. G., Michie, A. M., Erdogan, S., Zeng, L., O'Connel, J. C., Tobias, E. S., and MacPhee, I. Alternative splicing of the type-IVA cyclic AMP phosphodiesterase gene provides isoform variants with distinct N-terminal domains fused to a common, soluble catalytic unit: 'designer' changes in $V_{max}$, stability and membrane association. Biochem. Soc. Trans.: 23, 393–398, 1995.
48. Barnes, P. J.: Cyclic nucleotides and phosphodiesterases and airway function. Eur. Respir. J.: 8, 457–462, 1995.
49. Watchel, H. Species differences in behavioural effects of rolipram and other adenosine cyclic 3',5' phosphodiesterase inhibitors. J. Neural Transm. 56. 139–146, 1983.
50. Houslay, M. D., Scotland, G., Erdogan, S., Huston, E., Mackenzie, S., McCallum, J. F., McPhee, I., Pooley, L., Rena, G., Ross, A., Beard, M., Peder, A., Begg. F., Wilkinson, I., Yarwood, S., Ackerman, C., Houslay, E. S., Hoffman, R., Engels, P., Sullivan, M., and Bolger, G. Intracellular targeting, interaction with Src homology 3 (SH3) domains and rolipram-detected conformational switches in cAMP-specific PDE4A phosphodiesterase. Biochem. Soc. Trans. 25, 374381, 1997.
51. Kelly, J. J., Barnes, P. J., and Giembycz, M. A. Phosphodiesterase 4 in macrophages: relationship between cAMP accumulation, suppression of cAMP hydrolysis and inhibition of [3H]R-rolipram binding by selective inhibitors. Biochem. J. 318, 425–436, 1996.

TABLE I

Effect of cationic and anionic substitutions on PDE IVA high-affinity "switching" with respect to enzyme inhibition by (R)-rolipram.

|  | 10 mM | 30 mM | 100 mM | 150 mM | 300 mM |
|---|---|---|---|---|---|
| NaBr | 93 ± 22 | 132 ± 61 | 14 ± 4 | ND | 2 ± 0 |
| NaCl | 205 ± 59 | 291 ± 121 | ND | 4 ± 1 | 2 ± 0 |
| KCl | 176 ± 27 | 287 ± 92 | ND | 3 ± 1 | 3 ± 0 |
| Choline Chloride | 207 ± 40 | 194 ± 52 | ND | 3 ± 1 | 2 ± 0 |

TABLE II

Enzymatic properties of "high-affinity" and "low-affinity" flagged-PDE IVA conformers.

|  | 150 mM KCl 0 mg/ml HSA | 150 mM KCl 3 mg/ml HSA |
|---|---|---|
| Full-length PDE IVA | | |
| $K_m$ ($\mu$M) | 2.9 ± 0.4 | 4.8 ± 0.1 |
| $V_{max}$ ($\mu$m/mg/min) | 9.7 ± 0.2 | 4.8 ± 0 |
| (R)-Rolipram $IC_{50}$ (nM) | 111 ± 43 | 9 ± 3 |
| PDE IVA $met_{330}$ | | |
| $K_m$ ($\mu$M) | 2.6 ± 0.2 | 2.5 ± 0.2 |
| $V_{max}$ ($\mu$m/mg/min) | 6.7 ± 0.8 | 4.2 ± 0.5 |
| (R)-Rolipram $IC_{50}$ (nM) | 880 ± 0 | 2633 ± 738 |

TABLE III

Effect of Ionic Strength and Purified Human Serum Albumin on Binding of [$^3$H](R)-Rolipram to Purified Flagged-PDE IVA Enzyme.

| Assay Conditions | Bmax (fmol [$^3$H](R)-rolipram) | Stochiometry (fmol [$^3$H](R)-Rolipram/fmol PDE IVA enzyme) | Kd (nM) |
|---|---|---|---|
| 0 mM KCl | 30 (3) | 0.02 (0.0) | 0.4 (0.1) |
| 150 mM KCl | 63 (16) | 0.04 (0.01) | 0.4 (0.1) |
| 0 mM KCl + 3 mg/ml HSA | 150 (47) | 0.10 (0.03) | 0.8 (0.3) |
| 150 mM KCl + 3 mg/ml HSA | 240 (37) | 0.15 (0.03) | 0.4 (0.1) |

What is claimed is:

1. A method of assessing the capacity of an inhibitor of phosphodiesterase IV to inhibit phosphodiesterase IV, comprising the steps of:
   (a) preparing a cell free reaction mixture comprising:
      (1) soluble full length low-Km cAMP phosphodiesterase IVa enzyme;
      (2) test compound; and
      (3) a suitable enhancer of ionic strength;
   (b) incubating said reaction mixture; and
   (c) measuring the phosphodiesterase activity present in said reaction mixture.

2. The method according to claim 1 wherein the amount of low-Km cAMP phosphodiesterase IVa is that obtained from 0.003 $\mu$g/$\mu$l to 0.009 $\mu$g/$\mu$l cytosolic extract.

3. The method according to claim 2 wherein the amount of low-Km cAMP phosphodiesterase IVa is that obtained from about 0.006 $\mu$g/$\mu$l of cytosolic extract.

4. The method according to claim 1 wherein the amount of test compound is 1 $\mu$Mol/L to 0.3 nMol/L.

5. The method according to claim 1 wherein the enhancer of ionic strength is selected from the group consisting of $MgCl_2$, NaCl, Choline Chloride, NaBr and NaF.

6. The method according to claim 1 wherein the amount of enhancer of ionic strength used is 0 mM to 600 mM.

7. The method according to claim 6 wherein the amount of enhancer of ionic strength used is about 300 mM.

8. A system for stably expressing a soluble low-Km cAMP phosphodiesterase IV enzyme (PDE IV) comprising: CHO-K1 cells transfected with an expression vector for expressing human PDE IV DNA, the expression vector comprising pEE7.

9. The system according to claim 8 which comprises CHO-K1 cell line ATCC CRL 9618, an expression plasmid comprising vector pEE7 and human PDE IV cDNA.

10. The method of assessing the capacity of an inhibitor of phosphodiesterase IV to inhibit phosphodiesterase IV, comprising the steps of:
    (a) preparing a reaction mixture comprising:
       (1) CHO-K1 cells stably expressing full length low-Km cAMP phosphodiesterase IVa enzyme;
       (2) prostaglandin $I_2$; and
       (3) test compound;
    (b) incubating said reaction mixture; and
    (c) measuring the phosphodiesterase activity present in said reaction mixture.

11. The method according to claim 10 wherein the amount of CHO-K1 cells used is 0.1 million/ml to 0.4 minllion/ml.

12. The method according to claim 10 wherein the amount of CHO-K1 cells used is about 0.2 million/ml.

13. The method according to claim 12 wherein the amount of prostaglandin $I_2$ used is 5 $\mu$Mol/L to 20 $\mu$Mol/L.

14. The method according to claim 10 wherein the amount of prostaglandin $I_2$ used is about 10 $\mu$Mol/L.

15. The method according to claim 12 wherein the amount of test compound used is 0.0003 $\mu$M to 10 $\mu$M.

* * * * *